(12) United States Patent
Kuzelka et al.

(10) Patent No.: US 11,439,789 B2
(45) Date of Patent: Sep. 13, 2022

(54) SYSTEMS AND METHODS FOR AN INDUCTIVELY HEATED ANESTHETIC VAPORIZER

(71) Applicant: GE Precision Healthcare LLC, Milwaukee, WI (US)

(72) Inventors: Russell James Kuzelka, McFarland, WI (US); Joseph James Lacey, Cambridge, WI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 575 days.

(21) Appl. No.: 16/506,950

(22) Filed: Jul. 9, 2019

(65) Prior Publication Data
US 2021/0008326 A1 Jan. 14, 2021

(51) Int. Cl.
*A61M 16/18* (2006.01)
*A61M 16/20* (2006.01)
*A61M 16/10* (2006.01)

(52) U.S. Cl.
CPC .......... *A61M 16/18* (2013.01); *A61M 16/208* (2013.01); *A61M 16/106* (2014.02); *A61M 2202/0208* (2013.01); *A61M 2205/3334* (2013.01); *A61M 2205/3368* (2013.01); *A61M 2205/3379* (2013.01); *A61M 2205/368* (2013.01); *A61M 2205/50* (2013.01); *A61M 2205/52* (2013.01); *A61M 2206/20* (2013.01)

(58) Field of Classification Search
CPC .............. A61M 16/182; A61M 16/104; A61M 16/1035; A61M 16/109
See application file for complete search history.

(56) References Cited

U.S. PATENT DOCUMENTS

2012/0318263 A1 12/2012 Jones et al.
2016/0151600 A1* 6/2016 Heidschmidt ......... A61M 16/18
                                                        128/204.13

* cited by examiner

*Primary Examiner* — Margaret M Luarca
(74) *Attorney, Agent, or Firm* — McCoy Russell LLP

(57) ABSTRACT

Systems and methods are provided for delivering anesthetic agent to a patient. In one embodiment, an anesthetic vaporizer includes a vaporizing chamber configured to hold a liquid anesthetic agent, and an inductive heating element positioned exterior to the vaporizing chamber and housed within a gas-tight barrier, the inductive heating element operated to selectively heat a target.

20 Claims, 6 Drawing Sheets

US 11,439,789 B2

SYSTEMS AND METHODS FOR AN INDUCTIVELY HEATED ANESTHETIC VAPORIZER

FIELD

Embodiments of the subject matter disclosed herein relate to anesthesia systems, and more particularly, to anesthetic vaporizers.

BACKGROUND

During some medical procedures, such as surgical procedures, a patient may be placed under general anesthesia by administration of an anesthetic agent. In some examples, the anesthetic agent may be a volatile anesthetic agent that is administered to the patient via an anesthetic vaporizer. For example, the anesthetic vaporizer may induce and control vaporization of the volatile anesthetic agent from a liquid form. A carrier gas (e.g., a mixture of oxygen and fresh air) may flow into the vaporizer and blend (e.g., mix and converge) with the anesthetic agent vapors generated by the vaporizer. An amount of carrier gas flowing into the vaporizer may be adjusted by an operator of the vaporizer (e.g., an anesthesiologist) in order to adjust a ratio of carrier gas to anesthetic agents within the vaporizer. The mixed gases may then flow to the patient, where they may be introduced via inhalation, for example. The concentration of the anesthetic agent in the mixed gases may be controlled to ensure sufficient anesthetic agent is provided for patient comfort without compromising patient safety.

BRIEF DESCRIPTION

In one embodiment, a system for an anesthesia vaporizer includes a vaporizing chamber configured to hold a liquid anesthetic agent, and an inductive heating element positioned exterior to the vaporizing chamber and housed within a gas-tight barrier, the inductive heating element operated to selectively heat a target. In this way, an anesthesia vaporizer is provided that may accurately deliver anesthetic agent to a patient with a fast response time and stability at both low fresh gas flow rates (e.g., <1 liter per minute) and high fresh gas flow rates (e.g., between 10 and 15 liters per minute) without suffering a droop in output concentration and with a reduced risk of electrical sparking.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
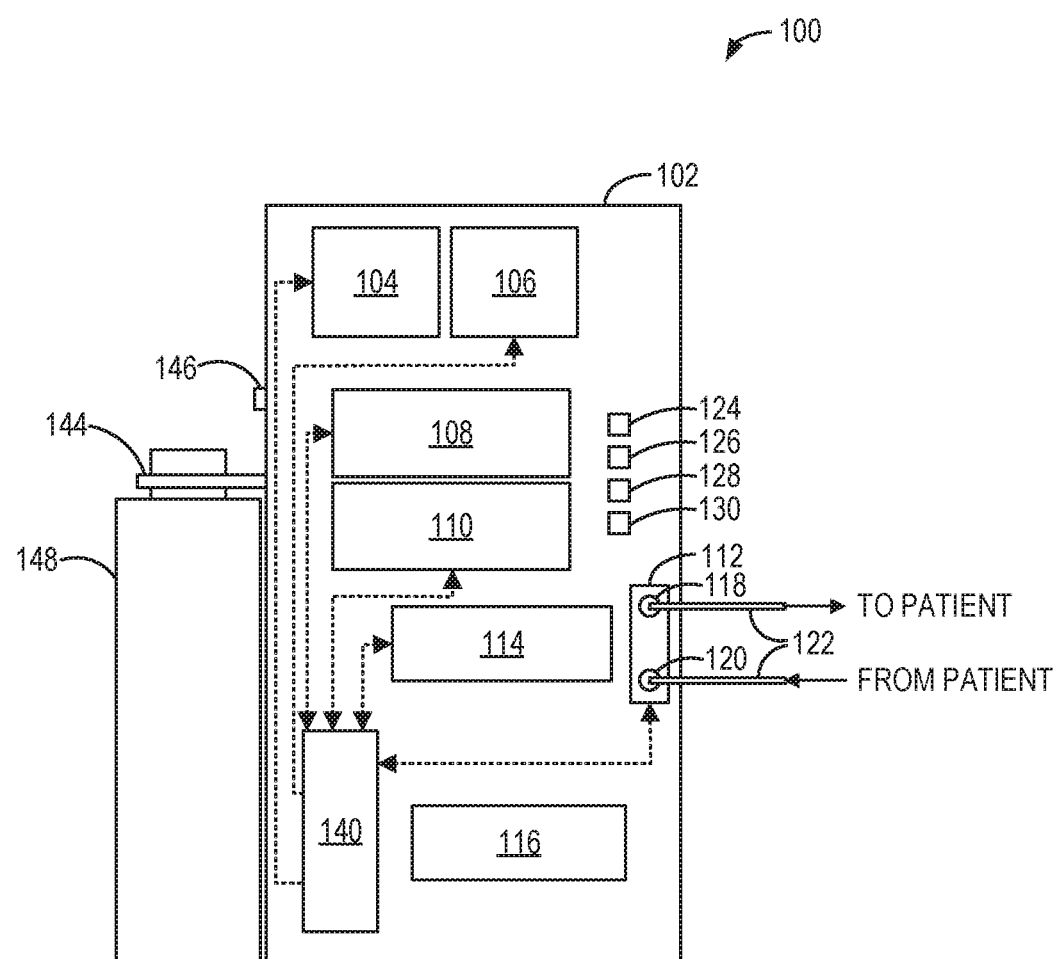
FIG. 1 schematically shows an exemplary embodiment of an anesthesia machine.

The following description relates to various embodiments of an anesthetic vaporizer system, which may be included in an anesthesia system. Fast, accurate, energy-efficient delivery of an anesthetic agent by an anesthetic vaporizer system may be challenging. For example, traditional anesthetic vaporizers systems may include pumps, compressors, pressurized sumps, pressurized secondary chambers, and/or injectors. As an example, liquid anesthetic agent in a sump may be bulk boiled by a heater to vaporize the anesthetic agent and pressurize the chamber. However, bulk boiling the liquid anesthetic agent increases an amount of energy consumed by the anesthetic vaporizer system due to the bulk thermal mass of the liquid anesthetic agent, which also creates a slow response to varying the temperature. In another example, a wick is used (cotton or plastic), where liquid anesthetic agent is absorbed by the wick and medical gas is passed over the wick surface. Agent is evaporated off from the wick and entrained in the gas stream. These systems are common and all suffer from slow response and droop, which is the inability to maintain high agent delivery rates in combination with high medical gas flow rates.

Further, the vaporizing chamber may be installed in a potentially oxygen-enriched location of the anesthetic vaporizer (e.g., having >25% $O_2$). For example, the location may become oxygen enriched due to the degradation of pneumatic seals (e.g., of oxygen gas carrying components) of the anesthetic vaporizer over its 10-15 year expected service life. Therefore, heaters used to bulk boil the liquid anesthetic agent within the vaporizing chamber and/or heat components of the vaporizing chamber may also be located in the oxygen enriched location. As such, there may be an increased risk of fire due to electrical sparking (e.g., of electronic components associated with the heater) and excessive heating (e.g., due to failures of insulation materials, etc.) in the oxygen enriched location.

Thus, according to embodiments disclosed herein, electronic components of an anesthetic vaporizer may be disposed within a gas-tight barrier, thereby isolating the electronic components from the potentially oxygen-enriched environment of a vaporizing chamber. The anesthetic vaporizer may include an inductive heating element, enabling the inductive heating element to be located within the gas-tight barrier and physically separated from the vaporizing chamber while still providing heat to components within the vaporizing chamber in order to vaporize liquid anesthetic agent housed therein. In some embodiments, the inductive heating element may heat a ferromagnetic collar wrapped around a heat pipe, and the heat pipe may be at least partially disposed within the liquid anesthetic agent in the vaporizing chamber to transfer heat from the inductively heated ferromagnetic collar to the liquid anesthetic agent. In other embodiments, the heat pipe may be disposed in a gas passage and configured to heat fresh gas flowing into the liquid anesthetic agent. In still other embodiments, the inductive heating element may heat a capillary pump disposed within the vaporizing chamber and at least partially comprised of a ferromagnetic material. Further, in some embodiments, gas (e.g., oxygen and fresh air) may be bubbled through the liquid anesthetic agent in the vaporizing chamber, but in other embodiments, gas may not be bubbled through the liquid anesthetic agent. Further, according to embodiments disclosed herein, the amount of anesthetic agent vapor output by the anesthetic vaporizer may be controlled by adjusting an amount of power supplied to the inductive heating element in a closed-loop fashion to accurately provide a desired amount of anesthesia to a patient.

The embodiments disclosed herein may provide several advantages. For example, the embodiments disclosed herein may provide a quick response time compared with bulk boiling due to a smaller thermal mass of the ferromagnetic component (e.g., the ferromagnetic collar or the capillary pump) and the inductive heating (versus conductive heating). Additionally, high concentrations of anesthetic agent at high flow rates may be maintained. Further, by using inductive heating instead of conductive heating, which relies on direct contact for efficient heat transfer, the heating element may be spatially separated from its target, enabling the heating element and other electronic components of the anesthetic vaporizer to be isolated in a gas-tight barrier. By isolating the electronic components in the gas-tight barrier, electrical sparking in the potentially oxygen-enriched environment of the anesthetic vaporizer may be reduced.

Figure 2:
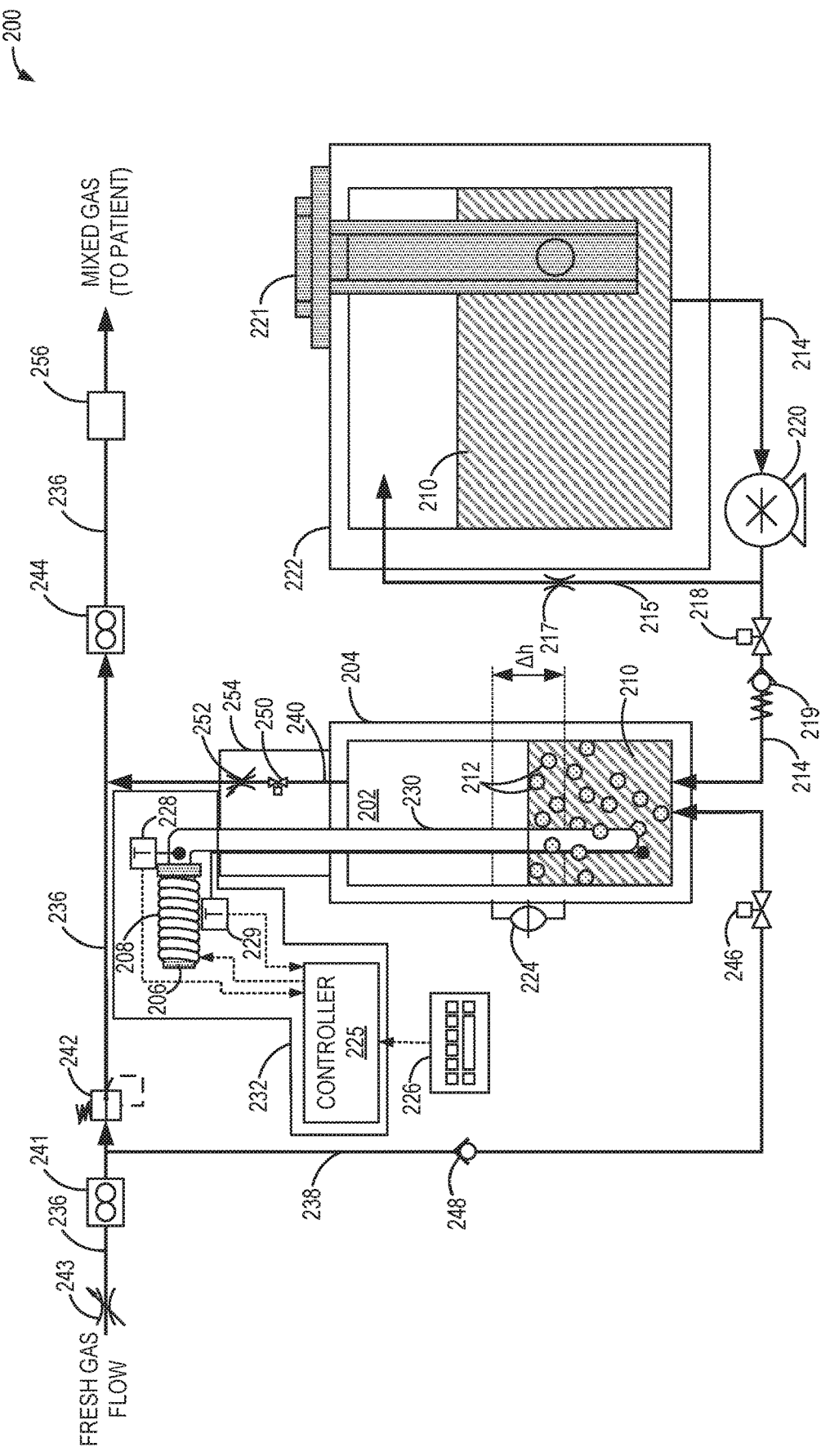
FIG. 2 schematically shows a first exemplary embodiment of an anesthetic vaporizer.
Figure 3:
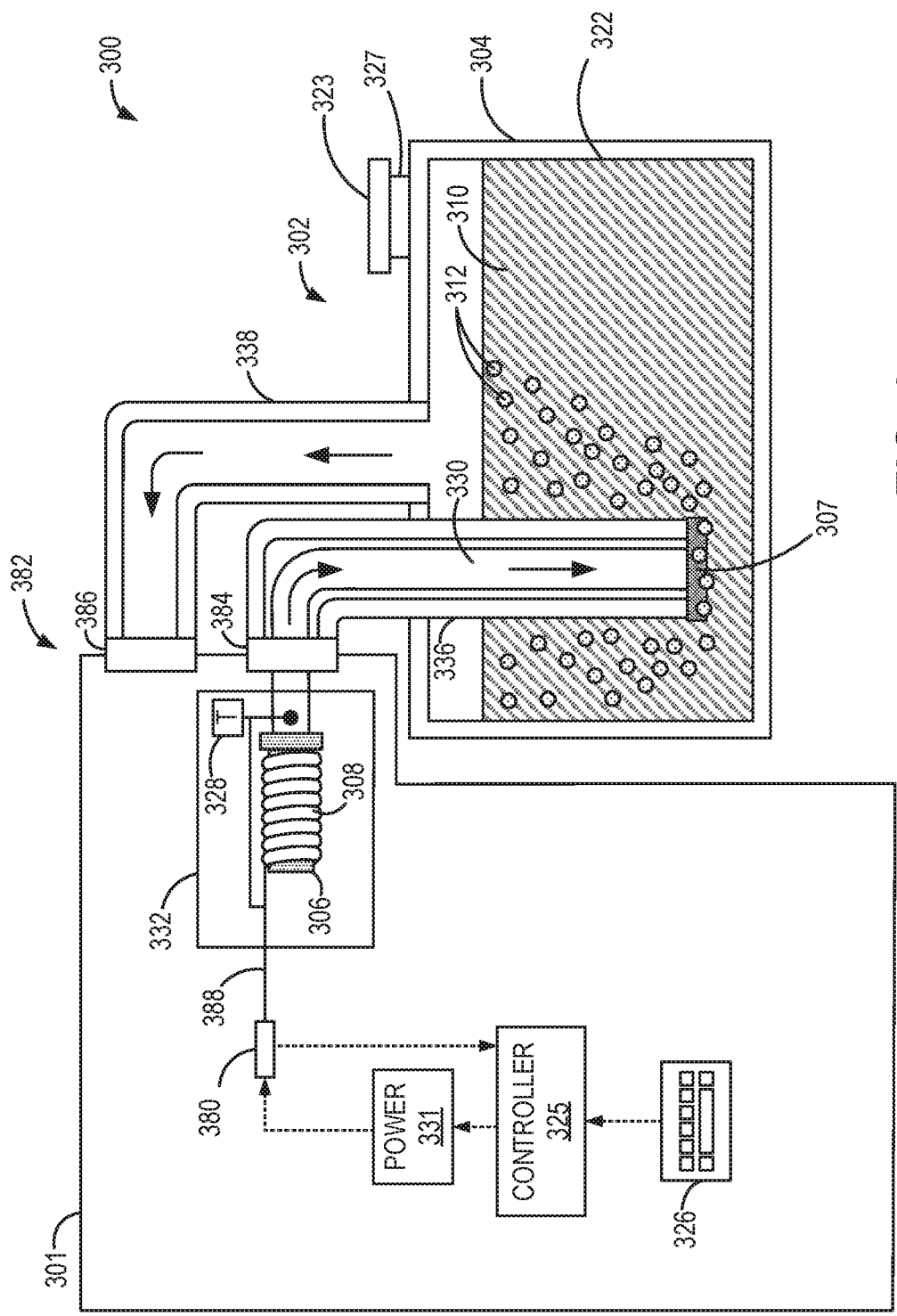
FIG. 3 schematically shows a second exemplary embodiment of an anesthetic vaporizer.
Figure 4:
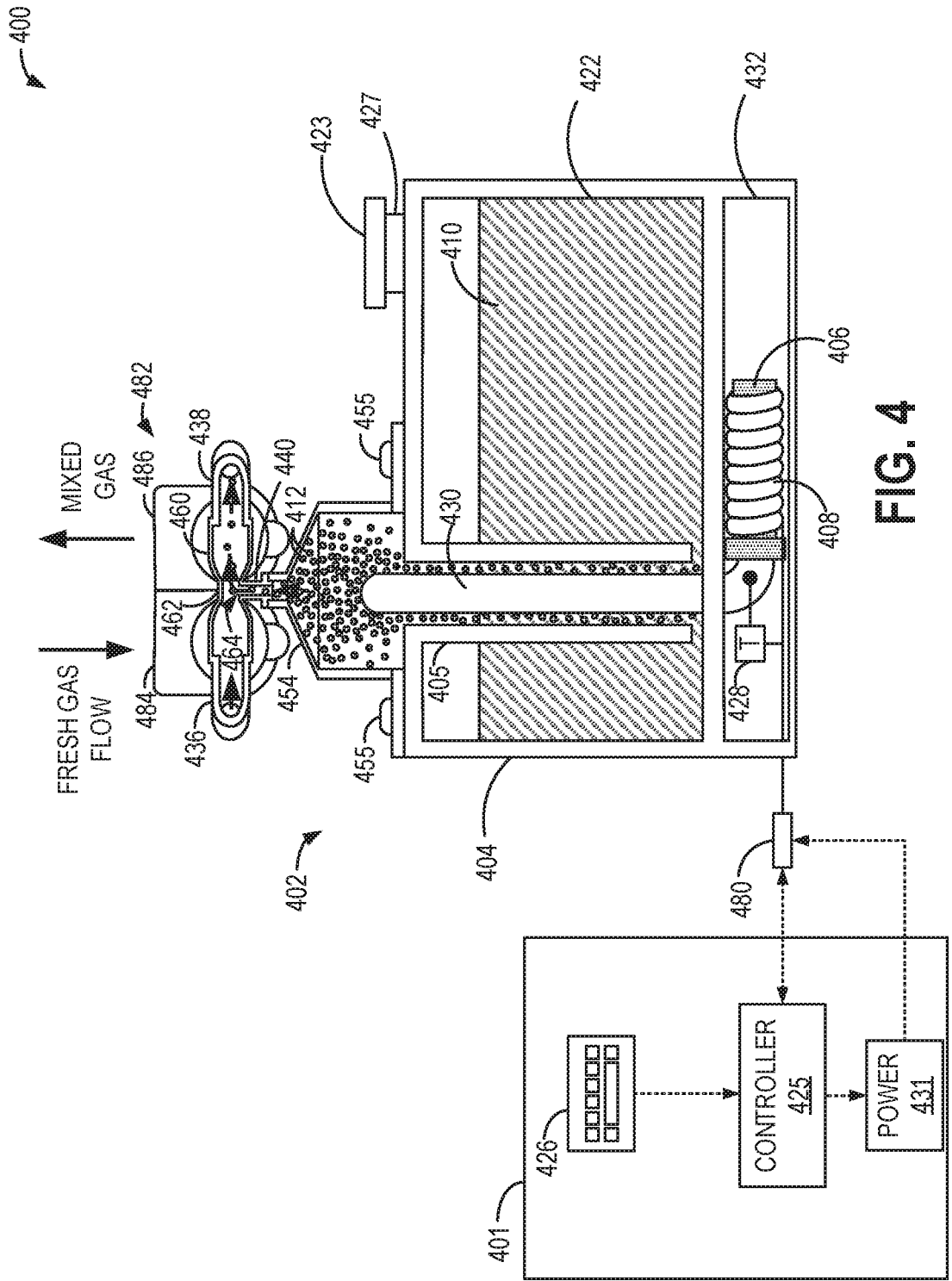
FIG. 4 schematically shows a third exemplary embodiment of an anesthetic vaporizer.
Figure 5:
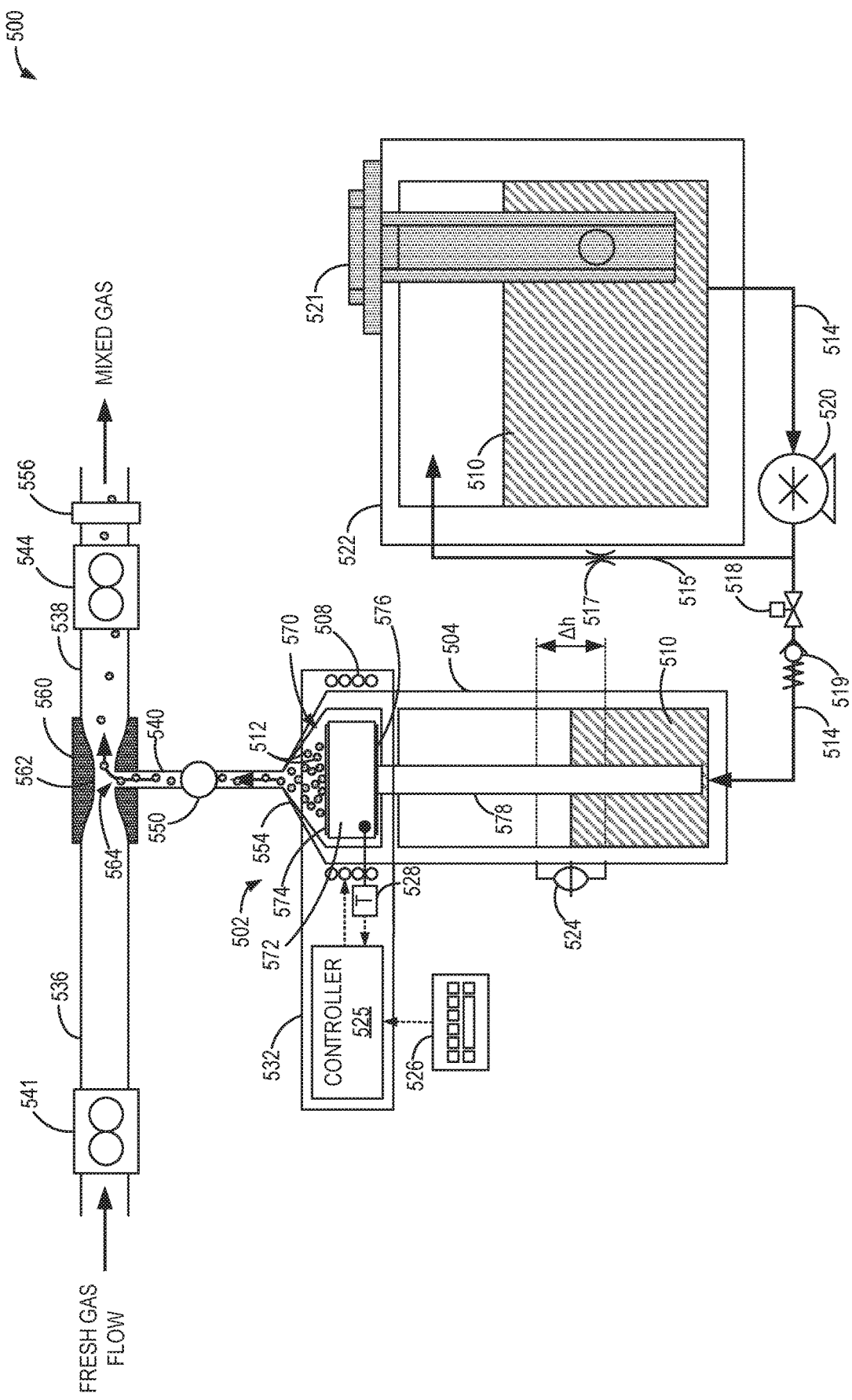
FIG. 5 schematically shows a fourth exemplary embodiment of an anesthetic vaporizer.

FIG. 1 schematically shows an exemplary embodiment of an anesthesia machine. FIGS. 2-5 each show an exemplary embodiment of an anesthetic vaporizer, which may be included in the anesthesia machine of FIG. 1. In particular, FIGS. 2-4 show different anesthetic vaporizer embodiments that each use a heat pipe for facilitating anesthetic agent vaporization, while FIG. 5 shows an anesthetic vaporizer embodiment that uses a capillary pump for facilitating anesthetic agent vaporization. The amount of vaporized anesthetic agent produced by the anesthetic vaporizer system may be controlled by adjusting an amount of power supplied to a heating element according to the example method of FIG. 6.

FIG. 1 schematically shows an example anesthesia machine 100. Anesthesia machine 100 includes a frame (or housing) 102. In some embodiments, frame 102 may be supported by casters, where the movement of the casters may be controlled (e.g., stopped) by one or more locks. In some examples, the frame 102 may be formed of a plastic material (e.g., polypropylene). In other examples, the frame 102 may be formed of a different type of material (e.g., metal, such as steel).

Anesthesia machine 100 also includes an anesthesia display device 104, a patient monitoring display device 106, a respiratory gas module 108, one or more patient monitoring modules, such as a patient monitoring module 110, a ventilator 112 (explained in more detail below), an anesthetic vaporizer 114, and an anesthetic agent storage bay 116. Anesthesia machine 100 may further include a main power indicator 124, a system activation switch 126 (which, in one example, permits gas flow when activated), an oxygen flush button 128, and an oxygen control 130. Example embodiments of anesthetic vaporizer 114 will be described below with respect to FIGS. 2-4. Anesthetic vaporizer 114 may vaporize the anesthetic agent and combine the vaporized anesthetic agent with one or more medical grade gases (e.g., oxygen, air, nitrous oxide, or combinations thereof), which may then be delivered to a patient.

Anesthesia machine 100 may additionally include an integrated suction, an auxiliary oxygen flow control, and various other components for providing and/or controlling a flow of the one or more medical grade gases to the patient. For example, anesthesia machine 100 includes one or more pipeline connections 146 to facilitate coupling of the anesthesia machine to pipeline gas sources. Additionally, anesthesia machine 100 includes a cylinder yoke 144, via which one or more gas-holding cylinders 148 may be coupled to the anesthesia machine. Thus, through the pipeline connection and/or cylinder connections, gas may be provided to the anesthesia machine, where the gas may include (but is not limited to) medical air, oxygen, nitrogen, and nitrous oxide. The gas that enters the anesthesia machine may mix with the vaporized anesthetic agent at the anesthetic vaporizer 114, as described above, before being supplied to a patient via the ventilator 112. The anesthesia machine may also include a serial port, a collection bottle connection, a cylinder wrench storage area, and an anesthesia gas scavenging system.

The ventilator 112 may include an expiratory check valve at an expiratory port 120, an expiratory flow sensor at the expiratory port 120, an inspiratory check valve at an inspiratory port 118, an inspiratory flow sensor at the inspiratory port 118, an absorber canister, a manual bag port, a ventilator release, an adjustable pressure-limiting valve, a bag/vent switch, and a bellows assembly. When a patient breathing circuit is coupled to the ventilator 112, breathing gases (e.g., air, oxygen, and/or nitrous oxide mixed with vaporized anesthetic agent) exit the anesthesia machine from the inspiratory port 118 and travel to the patient. Expiratory gases from the patient re-enter the anesthesia machine via the expiratory port 120, where carbon dioxide may be removed from the expiratory gases via the absorber canister.

During operation of the anesthetic vaporizer 114, an operator (e.g., an anesthesiologist) may adjust an amount of vaporized anesthetic agent that is supplied to the patient by adjusting a flow rate of gases from the gas source(s) (e.g., the pipeline gas supply) to the vaporizer. The flow rate of the gases from the gas source to the vaporizer may be controlled by the operator via one or more flow adjustment devices. For example, the flow adjustment devices may include analog and/or digital adjustment dials and/or other user input devices configured to actuate one or more flow control valves of anesthesia machine 100. In some embodiments, a first flow control valve may be positioned between the gas source(s) and the anesthetic vaporizer 114 and may be actuatable via the flow adjustment devices to a fully opened position, a fully closed position, and a plurality of positions between the fully opened position and the fully closed position.

Anesthesia machine 100 may additionally include one or more valves configured to bypass gases from the gas source(s) around the anesthetic vaporizer 114. The valves may enable a first portion of gases to flow directly from the gas source to the inspiratory port 118 and a second portion of gases to flow from the gas source through the anesthetic vaporizer 114 to mix with the vaporized anesthetic agents prior to flowing to the inspiratory port 118. By adjusting a ratio of the first portion of gases relative to the second portion of gases, the operator may control a concentration of vaporized anesthetic agent administered to the patient via the inspiratory port 118.

Further, the adjustments described above may be facilitated at least in part based on output from the respiratory gas module 108. The respiratory gas module 108 may be configured to measure various parameters of the gases exiting the vaporizer and/or being provided to the patient. For example, the respiratory gas module 108 may measure the concentrations of carbon dioxide, nitrous oxide, and the anesthetic agent provided to the patient. Further, the respiratory gas module 108 may measure respiration rate, minimum alveolar concentration, patient oxygen concentration, and/or other parameters. The output from the respiratory gas module 108 may be displayed via a graphical user interface on a display device (e.g., the anesthesia display device 104 and/or the patient monitoring display device 106) and/or used by a controller to provide closed-loop feedback control of the amount of anesthesia provided to the patient.

The ventilator 112 may optionally be coupled to a breathing circuit (not shown) including a plurality of tubes (e.g., gas passages) 122. The breathing circuit may be coupled between an airway of a patient (e.g., via a breathing mask positioned to enclose the mouth and/or nose of the patient or a tracheal intubation tube) and the inspiratory port 118. Gases (e.g., the one or more medical gases, or a mixture of the one or more medical gases and vaporized anesthetic agent from the anesthetic vaporizer 114) may flow from the inspiratory port 118, through the breathing circuit, and into the airway of the patient, where the gases are absorbed by the lungs of the patient. By adjusting the concentration of vaporized anesthetic agent in the gases as described above, the operator may adjust a degree to which the patient is anesthetized.

During conditions in which the breathing circuit is coupled to the airway, the anesthetic agent and/or fresh gas (without the anesthetic agent) may flow into the airway of the patent (e.g., through inhalation) via the inspiratory port 118 and the inspiratory check valve. As an example, the inspiratory check valve may open automatically (e.g., without input or adjustment by the operator) in response to inhalation by the patient and may close automatically in response to exhalation by the patient. Similarly, the expiratory check valve may open automatically in response to exhalation by the patient and may close automatically in response to inhalation by the patient.

In some embodiments, the operator may additionally or alternatively control one or more operating parameters of the anesthesia machine 100 via an electronic controller 140 of the anesthesia machine 100. Controller 140 includes a processor operatively connected to a memory. The memory may be a non-transitory computer-readable medium and may be configured to store computer executable code (e.g., instructions) to be processed by the processor in order to execute one or more routines, such as those described herein. The memory may also be configured to store data received by the processor. Controller 140 may be communicatively coupled (e.g., via wired or wireless connections) to one or more external or remote computing devices, such as a hospital computing system, and may be configured to send and receive various information, such as electronic medical record information, procedure information, and so forth. Controller 140 may also be electronically coupled to various other components of the anesthesia machine 100, such as the anesthetic vaporizer 114, the ventilator 112, the respiratory gas module 108, the anesthesia display device 104, and the patient monitoring display device 106.

The controller receives signals from the various sensors of the anesthesia machine 100 and employs the various actuators of the anesthesia machine 100 to adjust operation of the anesthesia machine 100 based on the received signals and instructions stored on the memory of the controller. For example, the flow of gases to the inspiratory port 118 may be controlled via an input device (e.g., keyboard, touchscreen, etc.) coupled to the electronic controller of the anesthesia machine 100. The controller 140 may display operating parameters of the anesthesia machine 100 via the anesthesia display device 104 and/or the patient monitoring display device 106. The controller may receive signals (e.g., electrical signals) via the input device and may adjust operating parameters of the anesthesia machine 100 in response (e.g., responsive) to the received signals.

As one example, the operator may input a desired concentration of the anesthetic agent to be delivered to the patient. A corresponding valve position of one or more valves of the anesthesia machine (e.g., a position of one or more bypass valves, as described above) may be empirically determined and stored in a predetermined lookup table or function in a memory of the controller. For example, the controller may receive the desired concentration of the anesthetic agent via the input device and may determine an amount of opening of the one or more valves corresponding to the desired concentration of the anesthetic agent based on the lookup table, with the input being the concentration of the anesthetic agent and the output being the valve position of the one or more valves. The controller may transmit an electrical signal to an actuator of the one or more valves in order to adjust each of the one or more valves to the corresponding output valve position. In some examples, the controller may compare the desired flow rate of gases to a measured flow rate of gases, such as measured by the inspiratory flow sensor, for example.

Controller 140 is shown in FIG. 1 for illustrative purposes, and it is to be understood that controller 140 may be located in various locations within, around, and/or remote from anesthesia machine 100. As an example, controller 140 may include multiple devices/modules that may be distributed throughout anesthesia machine 100. As such, controller 140 may include a plurality of controllers at various locations within anesthesia machine 100. As another example, additionally or alternatively, controller 140 may include one or more devices/modules that are external to anesthesia machine 100, located proximate to (e.g., in a same room) or remote from (e.g., a remote server) anesthesia machine 100. In each example, the multiple devices/modules may be communicatively coupled through wired and/or wireless connections.

Anesthetic vaporizers, such as anesthetic vaporizer 114 shown in FIG. 1, may employ various vaporizer engines (e.g., liquid to gas conversion components) to vaporize a liquid anesthetic agent. For example, the anesthetic vaporizer may use a flow-over vaporizer engine (in which a carrier gas flows over a top surface of a volatile liquid anesthetic agent), a wick-based vaporizer engine, a bubble-through vaporizer engine (in which the carrier gas is bubbled up through the liquid anesthetic agent), or a gas/vapor blender (in which heat is used to vaporize the liquid anesthetic agent, and the vapors are injected into a fresh gas flow). When the anesthetic agent undergoes a phase change from liquid to vapor, it absorbs energy, known as latent heat of vaporization. Therefore, flow-over, wick-based, and bubble-through vaporizers may also utilize a heating mechanism to provide energy for the latent heat of vaporization, at least in some examples. However, such methods may be inefficient and may also provide a source of electrical sparks in a potentially oxygen enriched area of the vaporizer.

Therefore, FIG. 2 shows a first exemplary embodiment of an anesthetic vaporizer 200, which may be included in an anesthesia machine (e.g., anesthesia machine 100 shown in FIG. 1). As one example, anesthetic vaporizer 200 may be anesthetic vaporizer 114 of FIG. 1. In particular, anesthetic vaporizer 200 is a bubble-through anesthetic vaporizer, including a vaporizing chamber 202 defined by a housing 204. A lower portion of vaporizing chamber 202 is shown holding a liquid anesthetic agent 210 that is supplied from a sump 222 via a conduit 214 and a pump 220. The liquid anesthetic agent 210 may be isoflurane, sevoflurane, or another liquid anesthetic agent of similar volatility, for example. Pump 220 may be a positive displacement pump, such as a reciprocating positive displacement pump, for example. Pump 220 may be selectively operated to deliver liquid anesthetic agent 210 from sump 222 to vaporizing chamber 202 in response to a command signal from a controller 225, as will be further described below. Controller 225 may be an electronic controller including a processor operatively connected to a memory. Controller 225 may be included in (e.g., a part of) or communicatively coupled to controller 140 shown in FIG. 1, for example. Furthermore, pump 220 may decouple vaporizing chamber 202 from sump 222, enabling sump 222 to be refilled while anesthetic vaporizer 200 is in use.

Conduit 214 may further include a shut-off valve 218 coupled between pump 220 and vaporizing chamber 202. For example, shut-off valve 218 may be an on-off valve, wherein shut-off valve 218 is actuated to an open (e.g., fully open) position that allows liquid anesthetic agent 210 to flow between sump 222 and pump 220 or a closed (e.g., fully closed) position that prevents (e.g., blocks) the flow of liquid anesthetic agent 210 between pump 220 and vaporizing chamber 202. Shut-off valve 218 may be actuated between the open and closed positions in response to a command signal from controller 225, for example. A liquid return line 215 may be coupled to conduit 214 between shut-off valve 218 and pump 220 to reduce pressure build up between shut-off valve 218 and pump 220, such as when shut-off valve 218 is closed. For example, excess liquid anesthetic agent 210 provided by pump 220 may be returned to sump 222 via liquid return line 215.

Conduit 214 may further include a check valve 219 coupled between shut-off valve 218 and vaporizing chamber 202. Check valve 219 may be a one-way, spring-loaded check valve that allows liquid anesthetic agent 210 to flow from pump 220 through open shut-off valve 218 to vaporizing chamber 202 and prevents liquid anesthetic agent 210 from flowing from vaporizing chamber 202 to pump 220. For example, check valve 219 may open automatically (e.g., without input or adjustment from the controller or operator) to flow the liquid anesthetic agent 210 toward vaporizing chamber 202 and close automatically to prevent the liquid anesthetic agent 210 from flowing from vaporizing chamber 202 back to pump 220. Further, liquid return line 215 may include a restriction 217, such as an orifice, to control flow through liquid return line 215. As a result, liquid anesthetic agent 210 may preferentially flow through check valve 219 instead of restriction 217 when shut-off valve 218 is open.

Controller 225 may selectively activate pump 220 to provide liquid anesthetic agent 210 from sump 222 to vaporizing chamber 202 responsive to a measurement received from a level sensor 224. For example, level sensor 224 may be an optical, ultrasonic, capacitive, float, or pressure-based level sensor configured to measure a level of liquid anesthetic agent 210 in vaporizing chamber 202. As one example, controller 225 may be configured to maintain the level of liquid anesthetic agent within a threshold range Δh. The threshold range Δh may be defined by a first, lower threshold level and a second, higher threshold level. The first threshold level may be a pre-determined, non-zero level of the liquid anesthetic agent that is calibrated to maintain a minimum level of liquid anesthetic agent 210 in vaporizing chamber 202 for desired vaporization properties. The second threshold level may be a pre-determined, non-zero level of the liquid anesthetic agent that is calibrated to prevent overfilling of vaporizing chamber 202 with liquid anesthetic agent 210 and minimize variation in the desired vaporization properties throughout the threshold range.

As an example, controller 225 may activate pump 220 in response to the level of anesthetic agent 210 reaching the first, lower threshold level and deactivate pump 220 responsive to the level of anesthetic agent 210 reaching the second, higher threshold level. As another example, additionally or alternatively, controller 225 may activate pump 220 at a duty cycle selected based on the measured level of the liquid anesthetic agent and/or a rate of change of the measured liquid anesthetic agent level to maintain a consistent level of the liquid anesthetic agent 210 in vaporizing chamber 202. For example, the controller may input the measured level of the liquid anesthetic agent and/or the rate of change into one or more look-up tables, algorithms, or functions and output the selected duty cycle. Controller 225 may then activate pump 220 at the selected duty cycle, which may be adjusted as the measured level of the liquid anesthetic agent and/or the rate of change of the measured level changes. For example, as the measured level increases, the duty cycle of pump 220 activation may decrease, and as the measured level decreases, the duty cycle of pump 220 activation may increase. In addition, a positive displacement stepper motor pump may also be used, where each positive displacement step of the pump is equivalent to a specified volume of anesthetic liquid. In this manner, the pump can be used to precisely fill the vaporization chamber and prevent overfill by recording the number of pump steps delivered. This approach may also be used to record a volume of liquid anesthetic agent 210 delivered to the vaporizing chamber 202, which may be used for anesthetic vaporizer run-time/maintenance analysis (service metrics), liquid leak detection, precise determination of amount of liquid anesthetic remaining and available for delivery, vaporization efficiency calculations, etc.

An upper portion of vaporizing chamber 202 (e.g., above a surface of liquid anesthetic 210) holds vapor, which may be a mixture of vaporized anesthetic agent and a carrier gas from a fresh gas flow. The fresh gas flow, and thus the carrier gas, may include one or more medical grade gases, such as oxygen, air, nitrous oxide, and combinations thereof. The fresh gas flow may be provided via one or more gas pipelines (e.g., via pipeline connections 416 shown in FIG. 1) and/or one or more gas-holding cylinders (e.g., via cylinder yoke 144 of FIG. 1). As shown in FIG. 2, the fresh gas flow may enter the anesthetic vaporizer 200 via a first gas passage 236. A first proportional valve 243 coupled to the first gas passage 236 may be adjusted by controller 225 to control an amount (or flow rate) of fresh gas flowing through the first gas passage 236. First proportional valve 243 may be a variable valve, such a continuously variable valve, that may be adjusted by controller 225 between a plurality of positions ranging from a fully open to a fully closed position. For example, as a degree of opening of first proportional valve 243 increases, an amount (e.g., flow rate) of fresh gas flowing through first gas passage 236 may increase.

A first mass flow sensor 241 may be coupled to first gas passage 236 downstream of first proportional valve 243 to measure a flow rate of the fresh gas flow entering the anesthetic vaporizer 200. For example, first mass flow sensor 241 may be an ultrasonic flow meter or a calorimetric (thermal) mass flow meter. A pressure regulator 242 coupled to first gas passage 236 may limit a pressure of the fresh gas flow downstream of pressure regulator 242. For example, pressure regulator 242 may be a pressure reducing valve such that a pressure of the fresh gas flow downstream of pressure regulator 242 does not exceed a pressure setpoint of the pressure regulator. Further, first mass flow sensor 241 may be used by controller 225 as part of the control system to provide feedforward control information upon a change in fresh gas flow into anesthetic vaporizer 200.

A second gas passage 238 branches off of the first gas passage between first mass flow sensor 241 and pressure reducing valve 242 to provide carrier gas (e.g., a portion of the fresh gas flow that flows to vaporizing chamber 202) to vaporizing chamber 202. For example, second gas passage 238 may pass through an opening in the bottom of housing 204, which may include a gas-tight seal, to flow the carrier into the liquid anesthetic agent 210 within vaporizing chamber 202. Thus, second gas passage 238 may serve as a gas inlet passage to vaporizing chamber 202. Further, pressure regulator 242 may control a gas pressure within second gas passage 238.

Second gas passage 238 may include one or more valves disposed therein. As shown in FIG. 2, second gas passage 238 includes a check valve 248 and a shut-off valve 246. Check valve 248 may be a one-way valve that allows the carrier gas to flow from the fresh gas flow to vaporizing chamber 202 and prevents the carrier gas from flowing from vaporizing chamber 202 toward first gas passage 236. For example, check valve 248 may open automatically (e.g., without input or adjustment from a controller or operator) to flow the carrier gas through second gas passage 238 toward vaporizing chamber 202 and close automatically to prevent gas flow toward first gas passage 236. In contrast, shut-off valve 246 may be an electronically or mechanically actuated valve that is operated responsive to input from controller 225 and/or an operator of anesthetic vaporizer 200 (e.g., an anesthesiologist). For example, shut-off valve 246 may be an on-off valve, where shut-off valve 246 is actuated to an open (e.g., fully open) position that allows gas flow through shut-off valve 246 or a closed (e.g., fully closed) position that prevents (e.g., blocks) gas flow through shut-off valve 246 in response to an appropriate command signal from controller 225.

The carrier gas delivered via second gas passage 238 flows through into vaporizing chamber 202 at or near the bottom of housing 204 to form a plurality of gas bubbles 212 within liquid anesthetic agent 210. The plurality of gas bubbles 212 pass through liquid anesthetic agent 210, becoming saturated with anesthetic agent as they rise to the surface of the liquid via mass transport of agent into the bubble. Vaporization of the liquid anesthetic agent is affected by bubble size, an amount of time the gas bubbles 212 spend in the liquid anesthetic agent 210 (which may be controlled for by controlling the level of the liquid anesthetic agent 210 in vaporizing chamber 202, as described above), and a temperature difference between each gas bubble 212 and the liquid anesthetic agent 210. Therefore, anesthetic vaporizer 200 includes a heat pipe 230 for providing heat to vaporizing chamber 202 while isolating heating electronics from the potentially oxygen-enriched environment of vaporizing chamber 202, as will be elaborated below.

Heat pipe 230 is partially disposed within vaporizing chamber 202. In the embodiment illustrated in FIG. 2, heat pipe 230 is bent (e.g., by approximately 90°) so that a first, horizontal portion of heat pipe is isolated from vaporizing chamber 202 via a barrier 232 while a second, vertical portion of heat pipe 230 crosses barrier 232 and extends through an opening in the top of housing 204 (which may include a gas-tight seal, for example) and into vaporizing chamber 202. Barrier 232 may form a gas-tight seal around the components disposed therein to isolate the components inside of barrier 232 from the components and environment outside of barrier 232. For example, barrier 232 may be a pneumatic barrier (e.g., a pneumatically sealed barrier) or may be hermetically sealed. In other embodiments, heat pipe 230 may extend into vaporizing chamber 202 at other locations, such as through the bottom of housing 204 (as will be described with respect to FIG. 4) or a side of housing 204. Thus, the positioning shown in FIG. 2 of heat pipe 230, barrier 232, and the other components disposed within barrier 232 relative to vaporizing chamber 202 is provided by way of example.

In the embodiment illustrated in FIG. 2, a bottom of the vertical portion of heat pipe 230 is submerged within the liquid anesthetic agent 210 held in vaporizing chamber 202. Thus, the vertical portion of heat pipe 230 is at least partially submerged within the liquid anesthetic agent 210. Heat pipe 230 may be comprised of copper, for example, or another material having a high thermal conductivity (e.g., nickel plated copper). The horizontal portion of heat pipe 230, contained within barrier 232, may be in direct contact with a ferromagnetic collar 206. In one embodiment, the horizontal portion of heat pipe 230 is friction-fit within ferromagnetic collar 206. Ferromagnetic collar 206 may be a thin-walled collar comprised of 400 series stainless steel, various grades of highly magnetic steel, iron, or other ferromagnetic materials (note non ferromagnetic materials can be used but at a substantially lower efficiency). A heating element 208 is positioned within barrier 232, external to vaporizing chamber 202, and may be coiled around a length of ferromagnetic collar 206, as shown. Further, heating element 208 may be in direct contact with (e.g., touching) ferromagnetic collar 206 or may not be in direct contact with ferromagnetic collar 206. In the embodiment of FIG. 2, heating element 208 is an induction heater including a power source, a high-current inductive heating coil, and an electronic oscillator that passes a high frequency (e.g., ~50 kHz) alternating current through the coil, creating a rapidly alternating magnetic field. The rapidly alternating magnetic field produced by heating element 208 penetrates ferromagnetic collar 206, generating eddy currents within ferromagnetic collar 206 to heat it via Joule heating and magnetic hysteresis losses. In this way, heating element 208 may selectively heat ferromagnetic collar 206 via induction heating without becoming hot itself and/or without directly heating additional components of anesthetic vaporizer 200 (e.g., heat pipe 230).

Induction heating of ferromagnetic collar 206 by heating element 208 may provide several advantages. For example, the heat is generated inside the ferromagnetic collar itself instead of via an external heat source via conduction. Thus, ferromagnetic collar 206 may be rapidly heated once heating element 208 is activated. Further, heating element 208 need not be in direct contact with ferromagnetic collar 206, reducing contamination between components. However, in other embodiments, heating element 208 may heat through conduction, and thus heating element 208 may be in direct contact with ferromagnetic collar 206 for efficient heat transfer.

As heat is generated within ferromagnetic collar 206 during the induction heating, the heat may be efficiently transferred to heat pipe 230 via conduction. Thus, selectively heating ferromagnetic collar 206 via induction heating by heating element 208 may also selectively heat the heat pipe 230. Heat pipe 230 transports the generated heat along its length such that a temperature of the entire heat pipe is substantially the same, and the temperature of the heat pipe is substantially the same as a temperature of ferromagnetic collar 206. In this way, the heat generated by the induction heating of ferromagnetic collar 206 by heating element 208 reaches vaporizing chamber 202 and the liquid anesthetic agent 210 contained therein to provide the latent heat of vaporization for the phase transition to the vapor form.

In one embodiment, controller 225 may adjust the amount of heat generated (e.g., via induction heating) to control an amount of vaporized anesthetic agent generated at vaporizing chamber 202. As an example, when a desired anesthetic agent flow rate (or concentration) to deliver to a patient is low, an amount of power provided to heating element 208 may be lower, preventing cool off from the latent heat of vaporization without increasing a temperature of the liquid anesthetic agent 210 and/or the gas bubbles 212. As another example, when the desired anesthetic agent flow rate (or concentration) is high, the amount of power provided to heating element 208 may be higher to facilitate production of additional vapor bubbles, such as through nucleated boiling off of the surface of heat pipe 230. Thus, all of the carrier gas that flows through vaporizing chamber 202 may be fully saturated with vapor from liquid anesthetic agent 210, even at high fresh gas flow rates (e.g., 10 L/min).

Vapor, such as the carrier gas that is saturated with vaporized anesthetic agent, may flow out of vaporizing chamber 202 via a third gas passage 240 (e.g., a vapor delivery passage). For example, third gas passage 240 may pass through an opening at or near a top of housing 204 and form a junction with first gas passage 236 to fluidically couple the upper portion of vaporizing chamber 202 with first gas passage 236. Third gas passage 240 is shown including a shut-off valve 250 and a second proportional valve 252 within a manifold 254. Shut-off valve 250 may be an electronically or mechanically actuated valve that is adjusted responsive to input from controller 225 and/or the operator. For example, shut-off valve 250 may be an on-off valve, wherein shut-off valve 250 is actuated to an open (e.g., fully open) position that allows gas flow through shut-off valve 250 or a closed (e.g., fully closed) position that prevents (e.g., blocks) gas flow through shut-off valve 250 in response to an appropriate command signal from controller 225. Shut-off valve 250 may be closed to quickly stop the supply of the anesthetic agent to a patient, for example. Second proportional valve 252 may be a variable valve, such a continuously variable valve, that may be adjusted by controller 225 between a plurality of positions ranging from a fully open to a fully closed position. For example, as a degree of opening of second proportional valve 252 increases, an amount (e.g., flow rate) of vapor flowing from vaporizing chamber 202 to first gas passage 236 (e.g., via third gas passage 240) may increase. Conversely, as the degree of opening of second proportional valve 252 decreases, the amount of vapor delivered from vaporizing chamber 202 to first gas passage 236 may decrease.

In the exemplary embodiment shown in FIG. 2, heat pipe 230 passes through manifold 254 on its way to vaporizing chamber 202. Thus, heat pipe 230 may additionally heat manifold 254 to prevent condensation of the vaporized anesthetic agent in shut-off valve 250 and second proportional valve 252. However, in other embodiments, manifold 254 may additionally or alternatively be heated by a dedicated manifold heater to maintain the valves at a substantially constant temperature, such as 40° C. in one non-limiting example.

Upstream of the junction with third gas passage 240 and downstream of the junction with second gas passage 238, first gas passage 236 carries a portion of the fresh gas flow called bypass gas. The bypass gas does not pass through vaporizing chamber 202. An amount of bypass gas flowing through first gas passage 236 may be adjusted by adjusting the fresh gas flow and may be limited by pressure regulator 242. The bypass gas, containing no vaporized anesthetic agent, and the vapor from vaporizing chamber 202, containing the carrier gas saturated with the vaporized anesthetic agent, mix at and downstream of the junction between first gas passage 236 and third gas passage 240. The mixed gas may then be delivered to the patient via an inspiratory limb of a breathing circuit (e.g., via inspiratory port 118 described with respect to FIG. 1). A second mass flow sensor 244 may be coupled to first gas passage 236 downstream of the junction with third gas passage 240 to measure a flow rate of the mixed gas exiting the anesthetic vaporizer 200. For example, second mass flow sensor 244 may be an ultrasonic flow meter or a calorimetric (thermal) mass flow meter. In the case of an ultrasonic flow metering architecture, the output anesthetic agent concentration may be calculated by the difference in the measured time of flight (TOF) between the upstream first mass flow sensor 241 and the downstream second mass flow sensor 244. Further, in some embodiments, an independent concentration sensor 256 may be coupled to first gas passage 236 downstream of the junction with third gas passage 240. Concentration sensor 256 may be any suitable sensor that is configured to measure a concentration of the anesthetic agent in the mixed gas. In one example, concentration sensor 256 may be an optical sensor that transmits light of a suitable wavelength (e.g., infrared) through the mixed gas and determines a concentration of the anesthetic agent based on an absorption of the light by the mixed gas. In other examples, the concentration sensor may be a carbon dioxide or oxygen sensor that measures the concentration of the anesthetic agent based on a displacement of the carbon dioxide or oxygen relative to a supplied concentration of carbon dioxide or oxygen in the fresh gas flow. Concentration sensor 256 may output a signal to controller 225 indicative of the measured concentration of the anesthetic agent (e.g., the concentration of the anesthetic agent vapor) in the mixed gas. Additionally, ultrasound may be used to measure a change in the gas speed of sound prior to and after introduction of vaporized anesthetic agent into the gas stream. The change in the speed of sound is a function of the anesthetic agent concentration, and thus, ultrasound may be used to determine the concentration of the anesthetic agent in the mixed gas.

In addition to receiving signals output by level sensor 224, concentration sensor 256, first mass flow sensor 241, and second mass flow sensor 244, controller 225 may receive additional signals, including a measured level of liquid anesthetic agent 210 within sump 222 from a level sensor 221. Level sensor 221 which may be an infrared level sensor, for example. Further, controller 225 may receive a measured temperature of heat pipe 230 from a temperature sensor 228 coupled to heat pipe 230 external to vaporizing chamber 202 and within barrier 232. The measured temperature of heat pipe 230 may give an indication of the temperature of the liquid anesthetic agent 210 within vaporizing chamber 202 in order to avoid overheating of the liquid anesthetic agent. In some embodiments, anesthetic vaporizer 200 may additionally or alternatively include a separate liquid anesthetic agent temperature sensor 229. As shown, an electronic component of the liquid anesthetic agent temperature sensor 229 may be located inside of the barrier 232 while a probe component of the liquid anesthetic agent temperature sensor 229 may descend into vaporizing chamber 202 along heat pipe 230 to reach the liquid anesthetic agent 210. In still other embodiments, the liquid anesthetic agent temperature sensor 229 may be mounted to a side wall of housing 204 to directly measure the liquid anesthetic agent temperature. Additional sensors may be positioned throughout anesthetic vaporizer 200, such as various pressure, temperature, and/or composition sensors.

Controller 225 receives the signals from the various sensors of FIG. 2, processes the input data, and employs the various actuators of FIG. 2 to adjust operation of anesthetic vaporizer 200 based on the received signals and instructions stored on a memory of the controller. For example, controller 225 may receive the measured concentration of the anesthetic agent from concentration sensor 256 and adjust a position of one or more of the first proportional valve 243 and the second proportional valve 252. As another example, controller 225 may receive the temperature of heat pipe 230 from temperature sensor 228 and/or the temperature of the liquid anesthetic agent 210 from liquid anesthetic agent temperature sensor 229 and adjust operation of heating element 208 based on the input measurements, as will be further described below with respect to FIG. 6.

Further, data may be input to controller 225 by the operator of anesthetic vaporizer 200 via a user input device 226 that is operationally connected to the controller and thus configured to transmit an input signal to controller 225 (e.g., via wired or wireless communication). User input device 226 may include one or more of a mouse, a keyboard, a voice input device, a touch input device for receiving a gesture from the operator, a motion input device for detecting non-touch gestures and other motions by the operator, and other comparable input devices, as well as associated processing elements capable of receiving user input from the operator.

Note that although one controller 225 is shown, controller 225 may include multiple devices/modules distributed at various locations within anesthetic vaporizer 200. As another example, additionally or alternatively, controller 225 may include one or more devices/modules that are external to anesthetic vaporizer 200. In each example, the multiple devices/modules may be communicatively coupled through wired and/or wireless connections.

In particular, by housing controller 225, temperature sensor 228, temperature sensor 229, and heating element 208 within barrier 232, electronic components of anesthetic vaporizer 200 may be isolated, such as via pneumatic separation, from a potentially oxygen-enriched environment that may form within anesthetic vaporizer 200. For example, the fresh gas flow may include oxygen gas at a higher concentration than air. Over time, pneumatic (e.g., gas-tight) seals within anesthetic vaporizer 200 may degrade, allowing the oxygen-enriched gas supplied from the fresh gas flow to leak out of the various gas delivery passages and into the interior of the anesthetic vaporizer. By sealing the electronic components in the barrier, any electrical sparking or excessive heating (e.g., due to degradation of heating element 208) will not occur in the oxygen-enriched environment, reducing further degradation of the anesthetic vaporizer.

Other anesthetic vaporizer systems are also possible that utilize a heat pipe and a barrier for isolating electronic component(s) of the anesthetic vaporizer to mitigate oxygen enrichment concerns. Turning now to FIG. 3, a second exemplary embodiment of an anesthetic vaporizer 300 is shown, which may be installed in an anesthesia machine 301 (which may be anesthesia machine 100 shown in FIG. 1, for example). Anesthetic vaporizer 300 may be similar to anesthetic vaporizer 200 of FIG. 2, including a heat pipe 330, a barrier 332, and a bubble-through architecture, but unlike anesthetic vaporizer 200 of FIG. 2, anesthetic vaporizer 300 is a self-contained disposable (or reusable) anesthetic agent cartridge. Similar to anesthetic vaporizer 200 of FIG. 2, electronic components of anesthetic vaporizer 300 may be housed within barrier 332, the benefits of which are described above with respect to FIG. 2.

Anesthetic vaporizer 300 includes a housing 304 that defines a sump 322. In one embodiment, particularly where anesthetic vaporizer cartridge 200 is designed for single-use applications, housing 304 is comprised of one or more plastics (e.g., polycarbonate, polypropylene, polyurethane) in order to reduce anesthetic vaporizer weight and cost. Such an embodiment may increase portability for usage in rural or field settings, for example, or any other setting outside of a traditional health care facility. In other embodiments, housing 304 may be at least partially comprised of metal. Sump 322 stores a liquid anesthetic agent 310 therein, which may be similar to liquid anesthetic agent 210 of FIG. 2. Vaporization occurs in the sump 322, and thus, the sump 322 is integrated into a vaporizing chamber 302 instead of anesthetic vaporizer 300 including a separate sump that supplies the liquid anesthetic agent to the vaporizing chamber (e.g., via a pump), such as in anesthetic vaporizer 200 of FIG. 2.

Sump 322 includes a fill port (or neck) 327 that is sealed by a cap 323. Anesthetic vaporizer 300 may be delivered to a point of use (e.g., a hospital or other healthcare facility) pre-filled with liquid anesthetic agent 310 in sump 322, and thus, sump 322 may be sealed by cap 323 by an agent manufacturer (e.g., at a factory). In one embodiment, cap 323 may include a mechanism that prevents removal of the cap outside of the factory so that sump 322 may only be filled/refilled by the agent manufacturer. As an example, anesthetic vaporizer 300 may be manufactured at low cost, enabling disposal at the hospital for single use implementation. Alternatively, anesthetic vaporizer 300 may be returned to the manufacturer for a limited number of factory refills of liquid anesthetic agent 310, after which anesthetic vaporizer 300 may be disposed of or rebuilt, as will be further described below. The number of fills may be tracked at the factory (e.g., based on a serial number of anesthetic vaporizer 300) via an electronic or physical counter, for example.

Sump 322 may be provided in a variety of volume capacities and with different liquid anesthetic agents stored therein, tailoring anesthetic vaporizer 300 to different medical procedures and uses. As one example, an operator of anesthesia machine 301 may select the particular cartridge-style anesthetic vaporizer 300 to use based on the anesthetic agent to be delivered and a length the procedure being performed. For example, the operator may select larger sump capacities for longer procedures (or procedures using high anesthetic agent flow rates) and smaller sump capacities for shorter procedures (or procedures using low anesthetic agent flow rates). Further, in some embodiments, sump 322 may have a large enough capacity to perform multiple procedures without the anesthetic vaporizer 300 having to be replaced (e.g., due to low liquid anesthetic agent 310 volume). Thus, sump 322 holds a self-contained supply of liquid anesthetic agent 210 that may not be replenished at the point of use.

Anesthetic vaporizer 300 may be a removable unit that is connected to and disconnected from gas passages of anesthesia machine 301 via a quick disconnect pneumatic system 382, which includes an input 384 and an output 386. Quick disconnect pneumatic system 382 pneumatically seals anesthetic vaporizer cartridge 300 from atmosphere so that when anesthetic vaporizer cartridge 300 is disconnected from the anesthesia machine 301 (e.g., quick disconnect pneumatic system 382 is not connected to a corresponding feature on the anesthesia machine), anesthetic vaporizer cartridge 300 is gas-tight and liquid-tight (e.g., completely sealed) stand-alone unit. Input 384 connects to a fresh gas flow from the anesthesia machine and enables fresh gas (e.g., oxygen, air, nitrous oxide, and combinations thereof) to flow from anesthesia machine 301 into vaporizing chamber 302 as carrier gas via a gas inlet passage 336. Heat pipe 330 extends within gas inlet passage 336 such that a wall defining gas inlet passage 336 is concentric around heat pipe 330. Further, gas inlet passage extends through an opening in housing 304 (which may include a liquid-tight seal, for example) and into sump 322 such that a first (e.g., top) portion of gas inlet passage 336 is external to sump 322 and a second (e.g., bottom) portion of gas inlet passage 336 is internal to sump 322 and configured to be at least partially submerged in the liquid anesthetic agent 310. Heat pipe 330 and gas inlet passage 336 do not directly contact each other, enabling the carrier gas to flow past heat pipe 330 within gas inlet passage 336 and into the liquid anesthetic agent 310 via a sparging filter 307, which is located near a bottom of sump 322 and is completely submerged within liquid anesthetic agent 310, to form a plurality of gas bubbles 312. Sparging filter 307 may cap the bottom of gas inlet passage 336, as shown, and may be comprised of metal or ceramic, for example. Sparging filter 307 may form a liquid-tight seal with the bottom surface of gas inlet passage 336 to allow gas to flow from gas inlet passage 336 to liquid anesthetic agent 310 while preventing the flow of liquid anesthetic agent 310 into gas inlet passage 336. The plurality of gas bubbles 312 pass through liquid anesthetic agent 310, becoming saturated with vaporized anesthetic agent, as they rise to the surface of the liquid.

Sparging filter 307 may increase an interfacial area between the carrier gas and liquid anesthetic agent 310 by decreasing a size of the gas bubbles 312, which in turn increases a rate of vaporization of liquid anesthetic agent 310. For example, gas bubbles 312 may be fine and/or micro bubbles. A geometry of sparging filter 307 may be selected to optimize an efficiency of the vaporization of the liquid anesthetic agent, which may be affected by the size of the gas bubbles 312 and the swirl of the gas bubbles 312, for example. In one embodiment, the size of the gas bubbles 312 may be selected to maximize the surface area of the fresh gas in contact with the liquid anesthetic agent 310 while reducing back pressure (e.g., a pressure drop across sparging filter 307) and to generate a defined and homogenous gas distribution. As an example, the large surface area-to-volume ratio of each small gas bubble 312 enables each gas bubble to become fully saturated with vapor of the liquid anesthetic agent 310.

In the embodiment shown in FIG. 3, heat pipe 330 bends (e.g., by approximately 90°) to enable heat pipe 330 to extend between barrier 332 and gas inlet passage 336. For example, a vertical portion of heat pipe 330 extends into gas inlet passage 336, while at least part of a horizontal portion of heat pipe 330 is isolated from vaporizing chamber 302 and gas inlet passage 336 via barrier 332. In the embodiment shown in FIG. 3, the horizontal portion of heat pipe 330 crosses barrier 332 and extends into gas inlet passage 336 before the bend.

Further, in the exemplary embodiment shown in FIG. 3, barrier 332 is located within anesthesia machine 301. For example, during installation of anesthetic vaporizer 300 into anesthesia machine 301, barrier 332 may be inserted into a compartment within anesthesia machine 301, and quick disconnect pneumatic system 382 may be connected to gas passages of anesthesia machine 301 to fluidically couple anesthesia machine gas flow to anesthetic vaporizer 300. Then, after use (or when sump 322 no longer holds enough liquid anesthetic agent 310 for completing a procedure), anesthetic vaporizer 300 may be disconnected from the anesthesia machine gas flow via quick disconnect pneumatic system 382, and barrier 332 may be removed from anesthesia machine 301. Anesthetic vaporizer 300 may then be returned to the manufacturer for refilling or refurbishing, and a different anesthetic vaporizer (holding the same or different liquid anesthetic agent at a same or different volume, depending on the next procedure to be performed) may be installed.

During operation, heat pipe 330 is heated via a heating element 308 and a ferromagnetic collar 306 positioned within barrier 332, which function similarly to heating element 208, ferromagnetic collar 206, and barrier 232 described above with respect to FIG. 2. Heat transfers from the hot heat pipe 330 to the colder carrier gas flowing past heat pipe 330. By activating heating element 308 to heat ferromagnetic collar 306 and thus heat pipe 330, the latent heat of vaporization for the phase transition from the liquid form of the anesthetic agent to the vapor form may be provided. Thus, all of the carrier gas that flows through vaporizing chamber 302 via gas inlet passage 336 may be fully saturated with vapor from liquid anesthetic agent 310, even at high fresh gas flow rates (e.g., 10 L/min).

Output 386 enables mixed gas comprising the carrier gas saturated with vaporized anesthetic agent to flow from vaporizing chamber 302 to anesthesia machine 301 via a gas outlet passage 338 (e.g., a vapor delivery passage). In one embodiment, output 386 may connect outlet passage 338 to a bypass gas flow of fresh gas at anesthesia machine 301, and the mixed gas may flow into the bypass gas flow before being delivered to a patient.

An electrical connector 380 may electronically couple heating element 308 to a power source 331 and/or a controller 325. As shown, electrical connector 380 may include a terminal positioned exterior to barrier 332 and wires 388 that extend into barrier 332 to form a permanent electrical connection with heating element 308. In other embodiments, power source 331 may be integrated in the disposable anesthetic vaporizer 300 unit and positioned within barrier 332. In some embodiments, a temperature sensor 328 for measuring a temperature of heat pipe 330 may be positioned within barrier 332 and may also be electronically coupled to controller 325 via electrical connector 380. In another embodiment, anesthetic vaporizer 300, particularly heating element 308, may be wirelessly connected to controller 325. Controller 325 may function similarly to controller 225 described above with respect to FIG. 2, such as to adjust the amount of power supplied to heating element 308 to adjust the concentration or flow rate of vaporized anesthetic agent produced, and may receive operator input via an HMI 326. In particular, controller 325 may receive an electronic feedback signal from temperature sensor 328 regarding the temperature of heat pipe 330 (which may be substantially the same temperature as ferromagnetic collar 306), process the input data, and adjust operation of heating element 308 based on the received signal and instructions stored on a memory of the controller. In still another embodiment, anesthetic vaporizer 300 may be manually controlled by the operator (e.g., via a dial) instead of being electronically controlled by controller 325, as also described above with respect to FIG. 2.

Controller 325 may be a dedicated (e.g., integrated) controller of anesthetic vaporizer 300 or may be a controller of the anesthesia machine 301. Controller 325 may not be included in the disposable portion of anesthetic vaporizer 300. For example, controller 325 may be reused with a new or refurbished anesthetic vaporizer when anesthetic vaporizer 300 has reached its limited number of factory refills, while sump 322, quick disconnect pneumatic system 382, gas inlet passage 336, and gas outlet passage 338 may be disposed of. In some examples, heat pipe 330, ferromagnetic collar 306, and heating element 308 may be reused in a new or refurbished anesthetic vaporizer, although the low costs of these components also renders them disposable, if desired.

Other disposable anesthetic vaporizer cartridge configurations that use an inductively heated heat pipe are also possible. Turning now to FIG. 4, a third exemplary embodiment of an anesthetic vaporizer 400 is shown, which may be installed in an anesthesia machine 401 (which may represent anesthesia machine 100 shown in FIG. 1, for example). As one example, anesthetic vaporizer 400 may be anesthetic vaporizer 114 of FIG. 1. Anesthetic vaporizer 400 may be similar to anesthetic vaporizer 200 of FIG. 2 and anesthetic vaporizer 300 of FIG. 3, including a heat pipe 430 and a barrier 432, but anesthetic vaporizer 400 does not utilize a bubble-through architecture. Further, similar to anesthetic vaporizer 300 of FIG. 3, anesthetic vaporizer 400 is a self-contained disposable (or reusable) anesthetic agent cartridge with electronic components housed within barrier 432, the benefits of which are described above with respect to FIG. 2.

Anesthetic vaporizer 400 includes a housing 404 that divides a sump 422 from barrier 432. Sump 422 stores a liquid anesthetic agent 410 therein, which may be similar to liquid anesthetic agent 210 of FIG. 2. Vaporization occurs in the sump 422, and thus, the sump 422 is integrated into a vaporizing chamber 402 instead of anesthetic vaporizer 400 including a separate sump that supplies the liquid anesthetic agent to the vaporizing chamber (e.g., via a pump), such as in anesthetic vaporizer 200 of FIG. 2. Sump 422 includes a fill port (or neck) 427 that is sealed by a cap 423. Anesthetic vaporizer 400 may be delivered to a point of use (e.g., a hospital or other healthcare facility) pre-filled with liquid anesthetic agent 410 in sump 422, and thus, sump 422 may be sealed by cap 423 by an agent manufacturer, such as described above with respect to FIG. 3.

Anesthetic vaporizer 400 may be a removable unit that is connected to and disconnected from gas passages of anesthesia machine 401 via a quick disconnect pneumatic system 482, which includes an input 484 and an output 486. Input 484 connects to a fresh gas flow from the anesthesia machine and, when connected, enables fresh gas (e.g., oxygen, air, nitrous oxide, and combinations thereof) to flow from the anesthesia machine to anesthetic vaporizer 300 via a gas inlet passage 436. Output 486 connects to a mixed gas flow of the anesthesia machine and, when connected, enables mixed gas (containing both fresh gas and anesthetic agent vapor 212) to flow from anesthetic vaporizer 400 to anesthesia machine 401 via a manifold 454 and a gas outlet passage 438, as will be elaborated below.

In the embodiment shown in FIG. 4, housing 404 comprises a gas generation passage 405 that extends into sump 422. Gas generation passage 405 is capped by a manifold 454 that is attached to sump 422 via a plurality of fasteners 455 (which may be screws or bolts, for example). Thus, manifold 454 may be removable from sump 422 while forming a gas-tight seal with sump 422 when attached. Further, in the embodiment shown in FIG. 4, heat pipe 430 is bent (e.g., by approximately 90°) so that a vertical portion of heat pipe 430 extends through an opening in housing 404 (which may include a liquid-tight seal, for example) and into sump 422, while a horizontal portion of heat pipe is isolated from sump 422 (and vaporizing chamber 402) via barrier 432. For example, the vertical portion of heat pipe 430 crosses barrier 432 and into liquid anesthetic agent 410 within sump 422 via a top wall of barrier 432 and a bottom wall of sump 422. Further, the vertical portion of heat pipe 430 extends into gas generation passage 405. For example, gas generation passage 405 may be concentric around heat pipe 430, and gas generation passage 405 does not extend to the bottom of sump 422, allowing liquid anesthetic agent 410 to flow into gas generation 405.

Heat pipe 430 is configured to be submerged in liquid anesthetic agent 410 within sump 422, particularly within gas generation passage 405, such that heat pipe 430 may be in direct contact with liquid anesthetic agent 410 within gas generation passage 405. During operation, heat pipe 430 is heated via a heating element 408 and a ferromagnetic collar 406 positioned within barrier 432, which function similarly to heating element 208, ferromagnetic collar 206, and barrier 232 described above with respect to FIG. 2. Heat transfers from the hot heat pipe 430 to the colder liquid anesthetic agent 410 within sump 422, and particularly within gas generation passage 405. By activating heating element 408 to heat ferromagnetic collar 406, and thus heat pipe 430, the latent heat of vaporization for the phase transition from the liquid form of the anesthetic agent to the vapor form may be provided. For example, localized boiling may occur in the liquid anesthetic agent 410 proximal to heat pipe 430, such as within gas generation passage 405, resulting in anesthetic agent vapor 412. This localized boiling may be more efficient than bulk-boiling the liquid anesthetic agent 410 within sump 422. Gas generation passage 405 then directs the anesthetic agent vapor 412 to manifold 454. Further, heat pipe 430 may at least partially extend within manifold 454 to heat manifold 454 and reduce or prevent vapor condensation within manifold 454.

The evolved anesthetic agent vapor 412 (e.g., vaporized anesthetic agent) may exit vaporizing chamber 402 via a vapor delivery passage 440 coupled to outlet manifold 454 and flow to a venturi 460. An inlet of venturi 460 is coupled to gas inlet passage 436, through which fresh gas flow is provided to venturi 460, and an outlet of venturi 460 is coupled to gas outlet passage 438. The fresh gas flow may be provided via one or more gas pipelines (e.g., via pipeline connections 146 shown in FIG. 1) and/or one or more gas-holding cylinders (e.g., gas-holding cylinder 148 of FIG. 1). Venturi 460 includes a tapered tube 462. The diameter of tapered tube 462 may gradually decrease until a minimum diameter is reached. For example, the minimum diameter may be maintained throughout a throat region 464 before gradually increasing again. The diameter of the inlet of venturi 460 may be the same as the diameter of the outlet of venturi 460, at least in some embodiments. Vapor delivery passage 440, which has a smaller diameter than each of the inlet of venturi 460 and the outlet of venturi 460, is shown coupled to tapered tube 462 of venturi 460 at throat region 464. As the fresh gas flows through tapered tube 462, a pressure drop occurs at throat region 464 that pulls the anesthetic agent vapor 412 into the fresh gas stream, resulting in mixed gas containing both the fresh gas from the fresh gas flow and the anesthetic agent vapor 412. For example, the mixed gas may be a homogenous mixture of the fresh gas and the anesthetic agent vapor 412. The mixed gas may then be delivered to the patient via an inspiratory limb of a breathing circuit of anesthesia machine 401 (e.g., via inspiratory port 118 described with respect to FIG. 1) via gas outlet passage 438 and output 486.

An electronic connection 480 may electronically couple heating element 408 to a controller 425. Controller 425 may be a dedicated controller of anesthetic vaporizer 400 or may be a controller of the anesthesia machine (e.g., controller 140 shown in FIG. 1). Thus, controller 425 may not be included in the disposable anesthetic agent cartridge of anesthetic vaporizer 400. In some embodiments, electronic connection 480 may also electronically couple heating element 408 to a power source 431, or power source 431 may be part of anesthetic vaporizer 400 and disposed within barrier 432. When power source 431 is included in anesthetic vaporizer 400, the power source may be a disposable or rechargeable battery, for example. In some embodiments, a temperature sensor 428 for measuring a temperature of heat pipe 430 may be disposed within barrier 432 and may also be electronically coupled to controller 425 via electronic connection 480. Controller 425 may function similarly to controller 225 described above with respect to FIG. 2, such as to adjust the amount of power supplied to heating element 408 to adjust the concentration or flow rate of vaporized anesthetic agent produced, and may receive operator input via an input device 426. In another embodiment, anesthetic vaporizer 400, particularly heating element 408, may be wirelessly connected to controller 425. In still another embodiment, anesthetic vaporizer 400 may be manually controlled by the operator (e.g., via a dial) instead of being electronically controlled by controller 425.

Prior to use, anesthetic vaporizer 400 may be installed in anesthesia machine 401 by fluidically coupling anesthesia machine gas flow to anesthetic vaporizer 400 via quick disconnect pneumatic system 482 and electronically coupling anesthetic vaporizer 400 to controller 425 (and/or the power source 431) via the electronic connection 480. Then, after use (or when sump 422 no longer holds enough liquid anesthetic agent 410 for completing a procedure), anesthetic vaporizer 400 may be disconnected from the anesthesia machine gas flow via quick disconnect pneumatic system 482 and disconnected from controller 425 via electronic connection 480. Anesthetic vaporizer 400 may then be returned to the manufacturer for refilling or refurbishing, and a different anesthetic vaporizer (holding the same or different liquid anesthetic agent at a same or different volume, depending on the next procedure to be performed) may be installed in anesthesia machine 401.

By providing the anesthetic vaporizer as a single-use cartridge that may be refilled at the anesthetic agent manufacturer instead of refilled at the point of use, such as anesthetic vaporizer 300 of FIG. 3 or anesthetic vaporizer 400 of FIG. 4, operator/clinician exposure to anesthetic agent is reduced by eliminating splashing/leaking of the anesthetic agent during refill. Additionally, usage costs and environmental pollution may be reduced by reducing anesthetic agent waste associated with refilling a vaporizer sump on-site via a refill bottle. Further still, the single-use cartridge may enable easier and more cost effective anesthetic agent delivery in rural areas, outside of a large healthcare facility setting.

Induction heating for facilitating anesthetic agent vaporization may be applied to other vaporizer engine types. Turning now to FIG. 5, a fourth exemplary embodiment of an anesthetic vaporizer 500 is shown, which may be included in an anesthesia machine (e.g., anesthesia machine 100 shown in FIG. 1). As one example, anesthetic vaporizer 500 may be anesthetic vaporizer 114 of FIG. 1. In particular, anesthetic vaporizer 500 is a wick-based anesthetic vaporizer, including a capillary pump 570 disposed within a vaporizing chamber 502 defined by a housing 504, a lower portion of which is shown holding a liquid anesthetic agent 510. The liquid anesthetic agent 510 may be isoflurane, sevoflurane, or another liquid anesthetic agent of similar volatility, for example. Capillary pump 570 includes a vaporization zone 572, which includes a vapor release area 574 and a liquid intake area 576, and a wick 578 that is at least partially submerged in the liquid anesthetic agent 510. As shown, wick 578 may extend toward a bottom of vaporizing chamber 502. In some embodiments, a bottom surface of wick 578 may touch an interior surface of housing 504 at the bottom of vaporizing chamber 502. In other embodiments, as shown, there may be a space between the interior surface of housing 504 and wick 578 such that wick 578 does not contact the interior surface of housing 504. Further, in some embodiments, a capillary tube bundle may be included in place of wick 578. The capillary tube bundle may be comprised of a plurality of thin capillary tubes that enable liquid anesthetic agent 210 to flow in the opposite direction of gravity via capillary action.

Capillary pump 570 may be at least partially comprised of one or more ferromagnetic materials. In one embodiment, vaporization zone 572 is comprised of a ferromagnetic material and wick 578 is comprised of a non-ferromagnetic material, such as ceramic or another non-ferromagnetic metal. In another embodiment, vaporization zone 572 and wick 578 are both comprised of a ferromagnetic material, which may be the same ferromagnetic material or a different ferromagnetic material for each. Wick 578 may be a single material or a stacked wick comprised of more than one material. In some embodiments where the capillary tube bundle is included in place of wick 578, the capillary tube bundle may be comprised of a ferromagnetic material (e.g., metal).

During operation, vaporization zone 572 is heated via a heating element 508. In the embodiment shown in FIG. 5, heating element 508 is an induction heater positioned exterior to vaporizing chamber 502. The rapidly alternating magnetic field produced by heating element 508 penetrates the ferromagnetic portions of capillary pump 570, particularly vaporization zone 572, generating eddy currents within vaporization zone 572 to heat it via Joule heating and magnetic hysteresis losses. As shown, heating element 508 may be positioned exterior to vaporizing chamber 502 at a vertical position that overlaps with a vertical position of vaporization zone 572 within vaporizing chamber 502. In particular, vaporization zone 572 is housed within an outlet manifold 554 of vaporizing chamber 502, and heating element 508 is positioned around outlet manifold 554. In this way, heating element 508 substantially surrounds the vaporization zone 572 (with housing 504 positioned intermediate the heating element 508 and vaporization zone 572) to selectively heat vaporization zone 572 (and other ferromagnetic components of capillary pump 570) via induction heating without becoming hot itself and/or without directly heating additional components of anesthetic vaporizer 500 (e.g., housing 504). Additionally, as a distance (e.g., radial distance and/or vertical distance) between the ferromagnetic components of capillary pump 570 and the heating element 508 increases, energy transfer efficiency decreases. Thus, the heating may be primarily targeted to the area of capillary pump 570 surrounded by heating element 508 (e.g., vaporization zone 572 in the embodiment shown in FIG. 5). Thus, a temperature gradient may form between the heated vaporization zone 572 and a bottom of wick 578. In embodiments including the ferromagnetic capillary tube bundle, heating element 508 may inductively heat a top portion of the capillary tube bundle, creating a temperature gradient between the top of the capillary tube bundle and the bottom of the capillary tube bundle.

Liquid anesthetic agent 510 is drawn through capillary pump 570 via capillary forces from a lower temperature area (e.g., the bottom of wick 578) to a higher temperature area (e.g., vaporization zone 572). That is, liquid anesthetic agent 510 is drawn up through a porous media (e.g., wick 578 or the capillary tube bundle) in thermal contact with a heated body (e.g., vaporization zone 572) and enters vaporization zone 572 via liquid intake area 576. The liquid anesthetic agent 510 is heated and converted to anesthetic agent vapor 512 in vaporization zone 572, and the anesthetic agent vapor 512 is released from vaporization zone 572 (and the capillary pump 570) at vapor release area 574. Heat travels opposite the fluid flow, from vaporization zone 572 toward wick 578, as a cooling flow of fresh liquid anesthetic agent 510 travels toward vaporization zone 572, resulting in a dynamic balance of heat flux, liquid flow, and evolved vapor.

In one embodiment, a controller 525 (which may be similar to controller 225 introduced in FIG. 2) may adjust the amount of heat generated at vaporization zone 572 (e.g., via induction heating) to control an amount of anesthetic agent vapor 512 generated. As an example, when a desired anesthetic agent flow rate (or concentration) to deliver to a patent is low, an amount of power provided to heating element 508 may be lower, and when the desired anesthetic agent flow rate (or concentration) is high, the amount of power provided to heating element 508 may be higher. The controller may receive the desired anesthetic agent flow rate (or concentration) from an operator via an input device 526, at least in one embodiment.

Additionally, a temperature sensor 528 may be coupled to vaporization zone 572 for measuring a temperature of vaporization zone 572. As shown, temperature sensor 528 may transmit a signal to controller 525 regarding the temperature of vaporization zone 572. In some embodiments, controller 525 may use the temperature signal received from temperature sensor 528 as a feedback signal for adjusting the amount of power provided to heating element 508. As an example, vaporization zone 572 may be heated to a desired temperature (via heating element 508) for providing the desired anesthetic agent flow rate (or concentration), with controller 525 determining the desired temperature by inputting the desired anesthetic agent flow rate (or concentration) into a look-up table, algorithm, or map stored in memory. Controller 525 may maintain vaporization zone 572 at the desired temperature based on the measured temperature received from temperature sensor 528, such as by increasing the amount of power supplied to heating element 508 responsive to the measured temperature being less than the desired temperature and decreasing the amount of power supplied to heating element 508 responsive to the measured temperature being greater than the desired temperature. However, in other embodiments, the amount of power provided to heating element 508 may be controlled without temperature feedback, and temperature sensor 528 may be omitted.

Further, the composition and structure of the materials comprising capillary pump 570, including pore size, pore size distribution, degree of porosity, and thermal conductivity, affect the resulting liquid permeability and capillary pressure. For example, materials having higher liquid permeability generally provide higher volume throughput, and materials with higher capillary pressure generally provide higher pressure vapor output. Thus, capillary pump 570 may be tailored for a specific application, such as for a particular anesthetic agent, for an anesthetic agent flow rate (or concentration) range, for a specific medical procedure, etc., to achieve desired pressure and flow effects. Thus, the amount of anesthetic agent vapor 512 generated by anesthetic vaporizer 500 may be precisely and simply controlled by both the selected capillary pump 570 composition and structure and the amount of power provided to heating element 508.

The evolved anesthetic agent vapor 512 (e.g., vaporized anesthetic agent) may exit vaporizing chamber 502 via a vapor delivery passage 540 coupled to outlet manifold 554 and flow to a venturi 560. An inlet of venturi 560 is coupled to a gas inlet passage 536, through which fresh gas flow is provided to venturi 560, and an outlet of venturi 560 is coupled to a gas outlet passage 538. The fresh gas flow may include one or more medical gases, such as oxygen, air, nitrous oxide, and combinations thereof. The fresh gas flow may be provided via one or more gas pipelines (e.g., via pipeline connections 146 shown in FIG. 1) and/or one or more gas-holding cylinders (e.g., gas-holding cylinder 148 of FIG. 1). Venturi 560 includes a tapered tube 562. As shown in FIG. 5, a diameter of tapered tube 562 may match that of gas inlet passage 536 where tapered tube 562 and gas inlet passage 536 are joined. The diameter of tapered tube 562 may gradually decrease until a minimum diameter is reached. For example, the minimum diameter may be maintained throughout a throat region 5564 before gradually increasing again to match that of gas outlet passage 538 where tapered tube 562 and gas outlet passage 538 are joined. The diameter of gas inlet passage 536 (and the inlet of venturi 560) may be the same as the diameter of gas outlet passage 538 (and the outlet of venturi 560), at least in some embodiments. Vapor delivery passage 540, which has a smaller diameter than each of gas inlet passage 536 and gas outlet passage 538, is shown coupled to tapered tube 562 of venturi 560 at throat region 564. As the fresh gas flows through tapered tube 562, a pressure drop occurs at throat region 564 that pulls the anesthetic agent vapor 512 into the fresh gas stream, resulting in mixed gas containing both the fresh gas from the fresh gas flow and the anesthetic agent vapor 512. For example, the mixed gas may be a homogenous mixture of the fresh gas and the anesthetic agent vapor 512. The mixed gas may then be delivered to the patient via an inspiratory limb of a breathing circuit (e.g., via inspiratory port 118 described with respect to FIG. 1).

One or more mass flow sensors may be included in anesthetic vaporizer 500. In the embodiment shown in FIG. 5, a first mass flow sensor 541 is coupled to gas inlet passage 536, and a second mass flow sensor 544 is coupled to gas outlet passage 538. First mass flow sensor 541 may transmit a signal to controller 525 indicative of a mass flow rate of the fresh gas within gas inlet passage 536 (e.g., upstream of venturi 560), and second mass flow sensor 544 may transmit a signal to controller 525 indicative of a mass flow rate of the mixed gas within gas outlet passage 538 (e.g., downstream of venturi 560). In one embodiment, the mass flow rate of the fresh gas and/or the mixed gas may be used by controller 525 to adjust the amount of power supplied to heating element 508 to provide the desired anesthetic agent concentration. One or both of first mass flow sensor 541 and second mass flow sensor 544 may be an ultrasonic flow meter or a calorimetric (thermal) mass flow meter. In the case of an ultrasonic flow metering architecture, the output anesthetic agent concentration may be calculated by the difference in the measured time of flight (TOF) between the upstream first mass flow sensor 541 and the downstream second mass flow sensor 544. Further, in some embodiments, an independent concentration sensor 556 may be coupled to gas outlet passage 538 downstream of venture 560. Concentration sensor 556 may be any suitable sensor that is configured to measure a concentration of the anesthetic agent in the mixed gas and output a corresponding signal to controller 525, as described with respect to concentration sensor 256 of FIG. 2.

In some embodiments, a valve 550 may be coupled between vaporizing chamber 502 and throat region 564 of venturi 560. In the embodiment shown in FIG. 5, valve 550 is coupled to vapor delivery passage 540; however, in other embodiments, valve 550 may be included in venturi 560. Valve 550 may be an on-off valve, such as a shut-off valve, where valve 550 is actuated between an "open" (e.g., fully open) position that allows vaporized anesthetic agent 512 to flow between vaporizing chamber 502 and throat region 564 and a "closed" (e.g., fully closed) position that prevents (e.g., blocks) the flow of vaporized anesthetic agent 512 between vaporizing chamber 502 and throat region 564. Valve 550 may be a mechanically or electronically actuated valve. As an example, valve 550 may be actuated between the open and closed positions in response to an appropriate command signal from controller 525. In other embodiments, valve 550 may be a variable valve, such as a proportional valve, that may be actuated to a plurality of positions between fully open and fully closed based on the command signal from controller 525. For example, controller 525 may adjust the position of valve 550 based on the desired anesthetic agent concentration to deliver to the patient, with a degree of opening of valve 550 increasing as the desired anesthetic agent concentration increases. Whether valve 550 is a shut-off valve or a proportional valve, valve 550 may be actuated to the fully closed position by controller 525 in response to input from the operator (e.g., via input device 526) to quickly stop the supply of the anesthetic agent to the patient.

Anesthetic vaporizer 500 further includes a barrier 532. Barrier 532 may be a pneumatic or hermetic barrier, for example, that forms a gas-tight seal around the components disposed therein, similar to barrier 232 described above with respect to FIG. 2. In the embodiment illustrated in FIG. 5, controller 525526, heating element 508, and an electronic component of temperature sensor 528 are housed within barrier 532 (whereas a probe component of temperature sensor 528 is coupled to vaporization zone 572 within outlet manifold 554). By housing controller 525, temperature sensor 528, and heating element 508 within barrier 532, electronic components of anesthetic vaporizer 500 may be isolated, such as via pneumatic separation, from a potentially oxygen-enriched environment that may form within anesthetic vaporizer 500, as elaborated above with respect to FIG. 2.

In another embodiment, barrier 532 may house only heating element 508. For example, barrier 532 may include potting of heating element 508, such as with silicone or epoxy potting material, and shielding the power wires to heating element 508 in a secondary plastic or metal tube. In this way, at least heating element 508 may be isolated from the potentially oxygen-enriched environment of anesthetic vaporizer 500.

The remaining components of anesthetic vaporizer 500 of FIG. 5 may function similarly to like components of anesthetic vaporizer 200 of FIG. 2. That is, a sump 522, a conduit 514, a pump 520, a liquid return line 515, a restriction 517, a shut-off valve 518, a check valve 519, a level sensor 521, and a level sensor 524 may function as described above for like-numbered components of FIG. 2 (e.g., sump 522 corresponds to sump 222 of FIG. 2). Additional sensors may be positioned throughout anesthetic vaporizer 500, such as various pressure, temperature, and/or composition sensors. Note that although anesthetic vaporizer 500 is shown in FIG. 5 as having a direct vapor injector architecture in which 100% anesthetic agent vapor 512 is injected into the fresh gas flow via venturi 560, in other embodiments, anesthetic vaporizer 500 includes a bypass vaporizer architecture in which a first portion of the fresh gas flow is routed through vaporizing chamber 502 as carrier gas, mixing with the anesthetic agent vapor 512 therein before joining a second, remaining (bypass) portion of the fresh gas flow.

Figure 6:
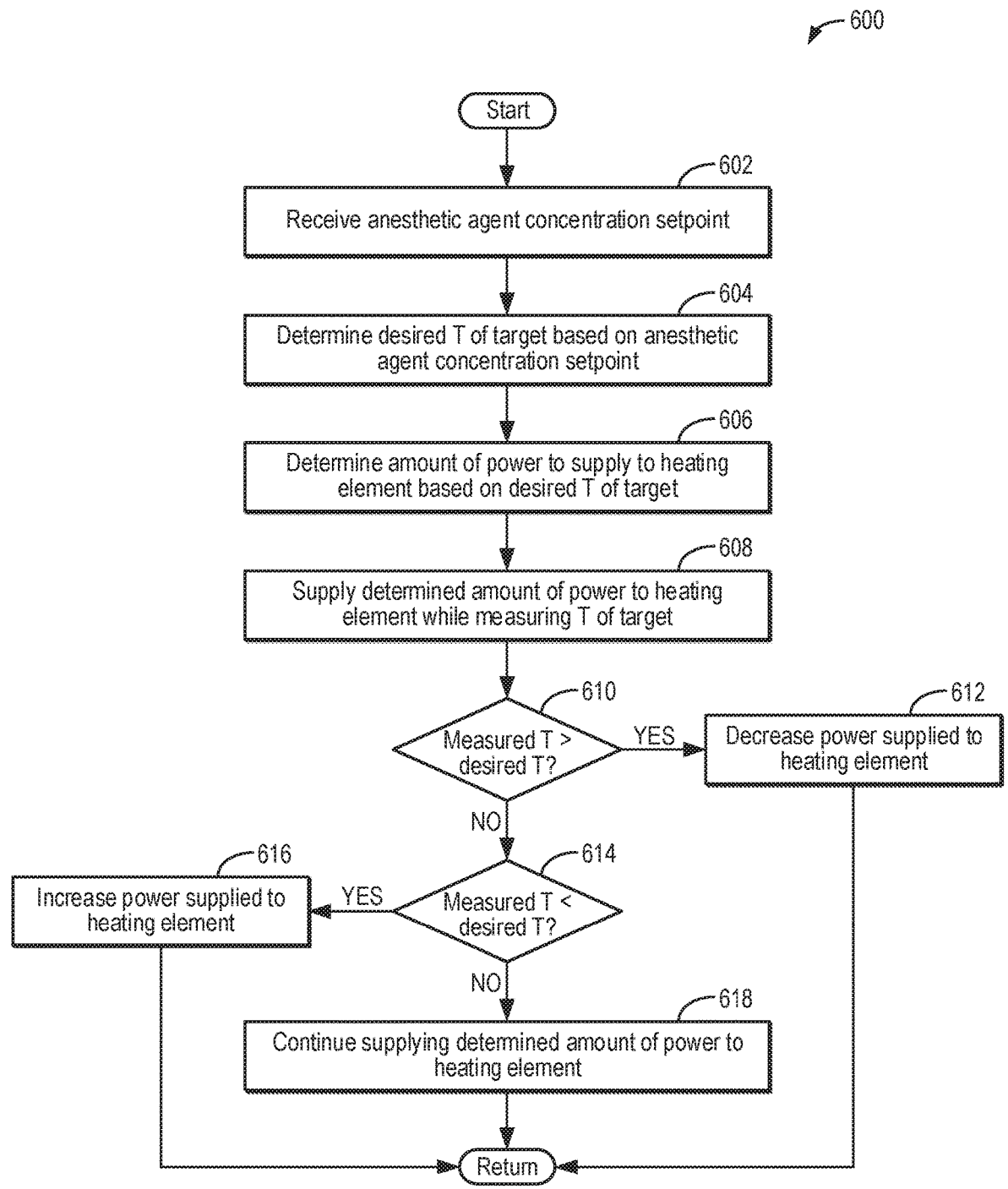
FIG. 6 is a flow chart illustrating an exemplary embodiment of a method for controlling an amount of power supplied to a heating element of an anesthetic vaporizer system.

Turning now to FIG. 6, a method 600 for operating a heating element of an anesthetic vaporizer, such as the anesthetic vaporizers of FIGS. 2-5, is shown. As one example, method 600 may be executed by a controller (e.g., any of controllers 225 of FIG. 2, controller 325 of FIG. 3, controller 425 of FIG. 4, and controller 525 of FIG. 5) in order to facilitate vaporization of a liquid anesthetic agent according to instructions stored in a memory of the controller and in conjunction with one or more sensors (e.g., temperature sensor 228 of FIG. 2, temperature sensor 328 of FIG. 3, temperature sensor 428 of FIG. 4, or temperature sensor 528 of FIG. 5) and actuators (e.g., heating element 208 of FIG. 2, heating element 308 of FIG. 3, heating element 408 of FIG. 4, or heating element 508 of FIG. 5). The heating element may be an inductive heating coil configured to heat a ferromagnetic collar and a heat pipe in a bubble-through vaporizer architecture (as described above with respect to FIGS. 2 and 3), configured to heat a ferromagnetic collar and a heat pipe for localized boiling (as described above with respect to FIG. 4), or configured to heat a vaporization zone of a capillary pump (as described above with respect to FIG. 5), for example. Adjusting the amount of heat generated via the heating element may adjust an amount of anesthetic agent output by the anesthetic vaporizer and thus, in one embodiment, method 600 may be used to control the amount of anesthetic agent output by the anesthetic vaporizer to a patient breathing circuit. In other embodiments, method 600 may be performed in conjunction with additional methods, such as valve control methods, to control the amount of anesthetic agent output by the anesthetic vaporizer.

At 602, an anesthetic agent concentration setpoint is received. The anesthetic agent may be any suitable volatile liquid anesthetic agent, such as desflurane, isoflurane, sevoflurane, or the like, or another medication that may be nebulized/inhaled, such as albuterol. The anesthetic agent concentration setpoint may be a percentage of the vaporized anesthetic agent per volume of a fresh gas/vaporized anesthetic agent mix provided to a patient. The anesthetic agent concentration setpoint, and, in some examples, the type of anesthetic agent used, may be obtained via user input to the controller (e.g., via input device 226 of FIG. 2, input device 326 of FIG. 3, input device 426 of FIG. 4, or input device 526 of FIG. 5) or via another suitable mechanism.

At 604, a desired temperature of a target is determined based on the anesthetic agent concentration setpoint. The target is a component of the anesthetic vaporizer that is heated when the heating element is operated, and the target includes a temperature sensor coupled thereto for providing temperature feedback to the controller. In embodiments where the anesthetic vaporizer includes a heat pipe and a ferromagnetic collar, the target may include the heat pipe and the ferromagnetic collar, and the desired temperature may include a desired temperature of the heat pipe. In embodiments where the anesthetic vaporizer includes a capillary pump, the target may include a vaporization zone of the capillary pump, and the desired temperature may include a desired temperature of the vaporization zone. In still other embodiments, the target may additionally or alternatively include the liquid anesthetic agent, and the desired temperature may include a desired temperature of the liquid anesthetic agent, such as where the anesthetic vaporizer includes a temperature sensor for measuring the temperature of the liquid anesthetic agent (e.g., temperature sensor 229 of FIG. 2). The controller may input the anesthetic agent concentration setpoint into a look-up table stored in memory, which may output the desired temperature of the target for the input anesthetic agent concentration setpoint, for example. As the anesthetic agent concentration setpoint increases, the desired temperature of the target that is output by the look-up table may increase, and as the anesthetic agent concentration setpoint decreases, the desired temperature of the target that is output by the look-up table may decrease. In some embodiments, the controller may further adjust the desired temperature of the target based on the type of anesthetic agent being used in order to account for different boiling points of the anesthetic agents. As an example, as a boiling point of the anesthetic agent increases, the desired temperature of the target may increase. Thus, the desired temperature may be a temperature setpoint selected to flow a desired amount of vaporized anesthetic agent from the vaporizing chamber to achieve the anesthetic agent concentration setpoint.

At 606, an amount of power to supply to the heating element is determined based on the desired temperature of the target. The heating element may include a variable frequency drive to vary the heating element voltage (or current) and frequency, such as via pulse-width modulation (PWM). Additionally or alternatively, the operation of the heating element may be phase-shifted from a resonance frequency to adjust (e.g., decrease) the heater output power. In one embodiment, the controller may determine a drive voltage and frequency (or duty cycle of voltage) to supply to the heating element by inputting the desired temperature into a look-up table, algorithm, or function, which may output the drive voltage and frequency (or duty cycle of voltage) for heating the target to the input desired temperature.

At 608, the determined amount of power is supplied to the heating element while measuring the temperature of the target. For example, the controller may provide voltage to the heating element at the drive voltage and frequency (or duty cycle of voltage) determined above at 606. At the same time, the temperature of the target may be measured by the temperature sensor coupled thereto to provide the temperature feedback signal to the controller.

In one embodiment, maximum power may be initially supplied to the heating element in order to heat the target from an ambient temperature to the desired temperature as quickly as possible, and thereby reduce an amount of time before the vaporized anesthetic agent can be delivered to the patient. As one example, a power source may output a maximum voltage and a maximum current to the heating element to supply maximum power to the heating element. As another example, resonant inductive coupling may be used, and the heating element may be operated at its resonance frequency to increase power transfer to the heating element, and thereby produce maximum heating of the target. The maximum power may continue to be supplied to the heating element until the measured temperature reaches or approaches (e.g., comes within a percentage of) the desired temperature, and then the power may be decreased from the maximum power to the amount of power determined at 606.

At 610, it is determined if the measured temperature is greater than the desired temperature. In one embodiment, the controller may include a proportional-integral-derivative controller that determines an error value between the desired temperature and the measured temperature based on proportional, integral, and derivative terms. In another embodiment, the controller may directly compare the measured temperature to the desired temperature. If the measured temperature is greater than the desired temperature (e.g., if the error value indicates that the measured temperature is greater than the desired temperature), method 600 proceeds to 612, and the power supplied to the heating element is decreased. For example, the controller may decrease the drive voltage and frequency (or duty cycle of voltage) supplied to the heating element responsive to the measured temperature being greater than the desired temperature in order to decrease the measured temperature to the desired temperature. Method 600 then returns to continue measuring the temperature of the target and adjusting the power supplied to the heating element based on the desired temperature relative to the measured temperature until the system is deactivated and anesthetic agent is no longer supplied to the patient.

Returning to 610, if the measured temperature is not greater than the desired temperature, method 600 proceeds to 614, and it is determined if the measured temperature is less than the desired temperature. If the measured temperature is less than the desired temperature (e.g., if the error value indicates that the measured temperature is less than the desired temperature), method 600 proceeds to 616, and the power supplied to the heating element is increased. For example, the controller may increase the drive voltage and frequency (or duty cycle of voltage) supplied to the heating element responsive to the measured temperature being less than the desired temperature in order to increase the measured temperature to the desired temperature. Method 600 then returns, as described above.

If instead the measured temperature is not less than the desired temperature at 614, then it may be assumed that the measured temperature is equal to the desired temperature. Method 600 proceeds to 618, and the determined amount of power continues to be supplied to the heating element. In this way, the target may be maintained at the desired temperature in order to provide the anesthetic agent at the anesthetic agent concentration setpoint. Method 600 then returns.

Thus, the systems and methods described herein provide for an inductively heated anesthetic vaporizer system. In some embodiments, the anesthetic vaporizer system may be a bubble-through anesthetic vaporizer, wherein carrier gas is heated by a heat pipe friction fit within an inductively heated ferromagnetic collar to provide latent heat of vaporization and increase the saturation of the carrier gas with anesthetic agent vapor. In other embodiments, the heat pipe may directly heat the liquid anesthetic agent to provide the latent heat of vaporization. In still other embodiments, the anesthetic vaporizer system may be a wick-based anesthetic vaporizer including a capillary pump at least partially comprised of a ferromagnetic material, wherein the inductive heating of the capillary pump heats liquid anesthetic drawn up the wick to facilitate vaporization. By heating the ferromagnetic anesthetic vaporizer components inductively, a quicker response time may be provided than bulk boiling the anesthetic agent and/or using conductive heating, and a smaller amount of energy may be consumed. Further, electronic components of the anesthetic vaporizer, including the inductive heating element, a controller, and electronic components of temperature sensors, may be housed within a gas-tight pneumatic barrier or hermetically sealed barrier to isolate the electronic components from a potentially oxygen-enriched environment of the anesthetic vaporizer, thereby reducing electrical sparking and the resulting component degradation. Further still, high concentrations of anesthetic agent at high flow rates may be maintained with high accuracy and simplified heater control.

A technical effect of housing electronic components of an anesthetic vaporizer within a gas-tight barrier is that the electronic components are isolated from a potentially oxygen-enriched environment of the anesthetic vaporizer.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A system for an anesthetic vaporizer, comprising:
   a vaporizing chamber configured to hold a liquid anesthetic agent; and
   an inductive heating element positioned exterior to the vaporizing chamber and housed within a gas-tight barrier, the inductive heating element operated to selectively heat a target component of the anesthetic vaporizer.

2. The system of claim 1, wherein the target component of the anesthetic vaporizer includes a heat pipe, a first portion of the heat pipe housed within the gas-tight barrier and a second portion of the heat pipe crossing the barrier and extending into the vaporizing chamber.

3. The system of claim 2, wherein the target component of the anesthetic vaporizer further includes a ferromagnetic collar in contact with the first portion of the heat pipe, the ferromagnetic collar housed within the gas-tight barrier, and the second portion of the heat pipe is configured to be at least partially submerged in the liquid anesthetic agent.

4. The system of claim 3, wherein the inductive heating element is coiled around a length of the ferromagnetic collar.

5. The system of claim 2, further comprising a gas inlet passage that fluidically couples the vaporizing chamber to a carrier gas portion of a medical gas, the gas inlet passage configured to flow the carrier gas portion into the liquid anesthetic agent in the vaporizing chamber.

6. The system of claim 1, wherein the target component of the anesthetic vaporizer includes a capillary pump, the capillary pump including a vaporization zone housed within an outlet manifold of the vaporizing chamber and one of a wick and a capillary tube bundle coupled to the vaporization zone and configured to be submerged in the liquid anesthetic agent in the vaporizing chamber, and wherein the vaporization zone is comprised of a ferromagnetic material.

7. The system of claim 6, further comprising a vapor delivery passage that fluidically couples the outlet manifold to a throat region of a venturi, an inlet of the venturi coupled to a fresh gas flow and an outlet of the venturi coupled to a patient breathing circuit.

8. The system of claim 1, further comprising a controller housed within the gas-tight barrier and storing executable instructions in non-transitory memory that, when executed, cause the controller to:
   adjust an amount of power provided to the heating element based on a desired temperature of the target component relative to a measured temperature of the target component, the desired temperature of the target determined based on an anesthetic agent concentration setpoint.

9. The system of claim 8, wherein the measured temperature of the target component is measured by a temperature sensor coupled to the target component, and the temperature sensor is housed within the gas-tight barrier.

10. The system of claim 8, wherein the instructions that cause the controller to adjust the amount of power provided to the heating element based on the desired temperature of the target component relative to the measured temperature of the target component include further instructions stored in non-transitory memory that, when executed, cause the controller to:
    determine a drive voltage and frequency of the heating element based on the desired temperature of the target component;
    operate the heating element at the determined drive voltage and frequency;
    increase the drive voltage and frequency from the determined drive voltage and frequency in response to the measured temperature of the target component being less than the desired temperature of the target component; and
    decrease the drive voltage and frequency from the determined drive voltage and frequency in response to the measured temperature of the target component being greater than the desired temperature of the target component.

11. A method for an anesthetic vaporizer, comprising:
    supplying power to an inductive heating element to heat a target at least partially disposed within a vaporizing chamber of the anesthetic vaporizer, the vaporizing chamber holding liquid anesthetic agent and the inductive heating element positioned within a gas-tight barrier that isolates the heating element from the vaporizing chamber; and adjusting the power supplied to the inductive heating element based on a temperature feedback signal.

12. The method of claim 11, wherein supplying power to the inductive heating element to heat the target comprises:

determining a desired temperature of the target based on a received anesthetic agent concentration setpoint;

determining an amount of power to supply to the inductive heating element to heat the target to the desired temperature; and supplying the determined amount of power to the inductive heating element.

13. The method of claim 12, wherein adjusting the power supplied to the inductive heating element based on the temperature feedback signal comprises:

receiving the temperature feedback signal from a temperature sensor coupled to the target;

decreasing the power supplied to the inductive heating element responsive to the temperature feedback signal indicating a temperature of the target is greater than the desired temperature of the target; and increasing the power supplied to the inductive heating element responsive to the temperature feedback signal indicating the temperature of the target is less than the desired temperature of the target.

14. The method of claim 12, wherein the target includes a heat pipe in contact with a ferromagnetic collar.

15. The method of claim 12, wherein a first portion of the heat pipe is friction fit within the ferromagnetic collar, the first portion of the heat pipe and the ferromagnetic collar housed within the gas-tight barrier, and a second portion of the heat pipe crosses the gas-tight barrier and extends into the liquid anesthetic agent held within the vaporizing chamber.

16. The method of claim 12, wherein the target includes a vaporization zone of a capillary pump, the vaporization zone comprised of a ferromagnetic material and the capillary pump further including a wick submerged in the liquid anesthetic agent held within the vaporizing chamber that delivers the liquid anesthetic agent to the vaporization zone.

17. A system for an anesthetic vaporizer, comprising:

a vaporizing chamber holding an anesthetic agent;

an inductive heating coil arranged exterior to the vaporizing chamber at a position that overlaps with a ferromagnetic component of the anesthetic vaporizer;

a vapor delivery passage that fluidically couples the vaporizing chamber to a patient breathing circuit;

a gas-tight barrier surrounding the inductive heating coil; and a controller housed within the gas-tight barrier, the controller storing executable instructions in non-transitory memory that, when executed, cause the controller to:

supply power to the inductive heating coil to heat the ferromagnetic component to a temperature setpoint selected to flow a desired amount of vaporized anesthetic agent from the vaporizing chamber to the patient breathing circuit; and adjust the power supplied to the inductive heating coil based on an electronic feedback signal.

18. The system of claim 17, wherein the ferromagnetic component includes a collar coupled to a heat pipe, a first portion of the heat pipe in direct contact with the collar and a second portion of the heat pipe configured to be submerged in the anesthetic agent in the vaporizing chamber, and wherein the electronic feedback signal is a temperature of the heat pipe measured by a temperature sensor coupled to the first portion of the heat pipe, the first portion of the heat pipe, the collar, and the temperature sensor housed within the gas-tight barrier.

19. The system of claim 17, wherein the ferromagnetic component includes a vaporization zone of a capillary pump, the vaporization zone housed within an outlet manifold of the vaporizing chamber, the outlet manifold positioned between the anesthetic agent in the vaporizing chamber and the vapor delivery passage, and the capillary pump further includes a wick configured to be submerged in the anesthetic agent in the vaporizing chamber that delivers anesthetic agent to the vaporization zone.

20. The system of claim 19, wherein in the electronic feedback signal is a temperature of the vaporization zone measured by a temperature sensor having a probe component coupled to the vaporization zone within the outlet manifold and an electronic component housed within the gas-tight barrier.

* * * * *